(12) United States Patent
Furuta et al.

(10) Patent No.: US 10,026,553 B2
(45) Date of Patent: *Jul. 17, 2018

(54) ORGANIC COMPOUND, CRYSTAL DIELECTRIC LAYER AND CAPACITOR

(71) Applicant: Capacitor Sciences Incorporated, Menlo Park, CA (US)

(72) Inventors: Paul Furuta, Sunnyvale, CA (US); Pavel Ivan Lazarev, Menlo Park, CA (US)

(73) Assignee: CAPACITOR SCIENCES INCORPORATED, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/919,337

(22) Filed: Oct. 21, 2015

(65) Prior Publication Data

US 2017/0117097 A1    Apr. 27, 2017

(51) Int. Cl.
| | |
|---|---|
| *H01G 4/14* | (2006.01) |
| *C07D 471/06* | (2006.01) |
| *C07D 471/22* | (2006.01) |
| *H01G 4/18* | (2006.01) |

(52) U.S. Cl.
CPC ............ *H01G 4/14* (2013.01); *C07D 471/06* (2013.01); *C07D 471/22* (2013.01); *H01G 4/18* (2013.01)

(58) Field of Classification Search
CPC ....................................................... H01G 4/14
USPC .......................................................... 546/27
See application file for complete search history.

(56) References Cited

U.S. PATENT DOCUMENTS

| | | |
|---|---|---|
| 3,407,394 A | 10/1968 | Hartke |
| 4,694,377 A | 9/1987 | MacDougall et al. |
| 4,702,562 A | 10/1987 | Scheuble et al. |
| 4,894,186 A | 1/1990 | Gordon et al. |
| 5,187,639 A | 2/1993 | Ogawa et al. |
| 5,248,774 A | 9/1993 | Dietz et al. |
| 5,312,896 A | 5/1994 | Bhardwaj et al. |
| 5,384,521 A | 1/1995 | Coe |
| 5,395,556 A | 3/1995 | Drost et al. |
| 5,466,807 A | 11/1995 | Dietz et al. |
| 5,514,799 A | 5/1996 | Varanasi et al. |
| 5,581,437 A | 12/1996 | Sebillotte et al. |
| 5,583,359 A | 12/1996 | Ng et al. |
| 5,679,763 A | 10/1997 | Jen et al. |
| 5,739,296 A | 4/1998 | Gvon et al. |
| 5,742,471 A | 4/1998 | Barbee et al. |
| 5,840,906 A | 11/1998 | Zoltewicz et al. |
| 5,880,951 A | 3/1999 | Inaba |
| 6,049,428 A | 4/2000 | Khan et al. |
| 6,174,394 B1 | 1/2001 | Gvon et al. |
| 6,282,081 B1 | 8/2001 | Takabayashi et al. |
| 6,294,593 B1 | 9/2001 | Jeng et al. |
| 6,341,056 B1 | 1/2002 | Allman et al. |
| 6,391,104 B1 | 5/2002 | Schulz |
| 6,426,861 B1 | 7/2002 | Munshi |
| 6,501,093 B1 | 12/2002 | Marks |
| 6,583,284 B1 | 6/2003 | Sidorenko et al. |
| 6,617,830 B2 | 9/2003 | Nozu et al. |
| 6,798,642 B2 | 9/2004 | Decker et al. |

(Continued)

FOREIGN PATENT DOCUMENTS

| | | |
|---|---|---|
| CN | 103261370 A | 8/2013 |
| CN | 203118781 U | 8/2013 |

(Continued)

OTHER PUBLICATIONS

Chao-Hsien Hoa et al., "High dielectric constant polyaniline/ poly(acrylic acid) composites prepared by in situ polymerization", Synthetic Metals, vol. 158, pp. 630-637 (2008).

Henna Russka et al., "A Density Functional Study on Dielectric Properties of Acrylic Acid Crafted Polypropylene", The Journal of Chemical Physics, vol. 134, p. 134904 (2011).

International Search Report and Written Opinion for International Application No. PCT/US2016/019641, dated Jul. 12, 2016.

International Search Report and Written Opinion for International Application No. PCT/US2016/033628, dated Sep. 1, 2016.

(Continued)

*Primary Examiner* — Taofiq A Solola
(74) *Attorney, Agent, or Firm* — JDI Patent; Joshua Isenberg; Robert Pullman

(57) ABSTRACT

The present disclosure provides an organic compound characterized by electronic polarizability and having a following general structural formula:

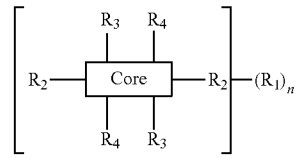

where Core is an aromatic polycyclic conjugated molecule, $R_1$ is group providing solubility of the organic compound in an organic solvent, n is 1, 2, 3, 4, 5, 6, 7 or 8, $R_2$ is substitute located in apex positions, R3 and R4 are substitutes located in side (lateral) positions and, the core has flat anisometric form and the $R_2$ substitutes are selected from hydrogen and electrophilic groups (acceptors) and $R_3$ substitutes and $R_4$ substitutes are independently selected from hydrogen and nucleophilic groups (donors) or vice versa $R_3$ substitutes and $R_4$ substitutes are independently selected from hydrogen and nucleophilic groups (donors) and $R_2$ substitutes are selected from hydrogen and electrophilic groups (acceptors), and the substitutes $R_2$, $R_3$ and $R_4$ cannot all be hydrogen.

7 Claims, 1 Drawing Sheet

(56) References Cited

U.S. PATENT DOCUMENTS

| | | |
|---|---|---|
| 7,025,900 B2 | 4/2006 | Sidorenko et al. |
| 7,026,019 B2 | 4/2006 | Dutova et al. |
| 7,033,406 B2 | 4/2006 | Weir et al. |
| 7,045,177 B2 | 5/2006 | Dutova et al. |
| 7,160,485 B2 | 1/2007 | Nazarov et al. |
| 7,211,824 B2 | 5/2007 | Lazarev |
| 7,460,352 B2 | 12/2008 | Jamison et al. |
| 7,466,536 B1 | 12/2008 | Weir et al. |
| 7,498,689 B2 | 3/2009 | Mitani et al. |
| 7,579,709 B2 | 8/2009 | Goetz et al. |
| 7,625,497 B2 | 12/2009 | Iverson et al. |
| 7,750,505 B2 | 7/2010 | Ichikawa |
| 7,808,771 B2 | 10/2010 | Nguyen et al. |
| 7,837,902 B2 | 11/2010 | Hsu et al. |
| 7,888,505 B2 | 2/2011 | Doutova et al. |
| 7,893,265 B2 | 2/2011 | Facchetti et al. |
| 7,910,736 B2 | 3/2011 | Koenemann et al. |
| 7,947,199 B2 | 5/2011 | Wessling |
| 8,143,853 B2 | 3/2012 | Jestin et al. |
| 8,222,074 B2 | 7/2012 | Lazarev |
| 8,231,809 B2 | 7/2012 | Pschirer et al. |
| 8,236,998 B2 | 8/2012 | Nagata et al. |
| 8,344,142 B2 | 1/2013 | Marder et al. |
| 8,404,844 B2 | 3/2013 | Kastler et al. |
| 8,527,126 B2 | 9/2013 | Yamamoto et al. |
| 8,552,179 B2 | 10/2013 | Lazarev |
| 8,818,601 B1 | 8/2014 | V et al. |
| 8,895,118 B2 | 11/2014 | Geivandov et al. |
| 8,929,054 B2 | 1/2015 | Felten et al. |
| 8,938,160 B2 | 1/2015 | Wang |
| 9,056,676 B1 | 6/2015 | Wang |
| 9,733,406 B2 | 8/2017 | Doutova et al. |
| 2002/0027220 A1 | 3/2002 | Wang et al. |
| 2002/0048140 A1 | 4/2002 | Gallay et al. |
| 2003/0026063 A1 | 2/2003 | Munshi |
| 2003/0102502 A1 | 6/2003 | Togashi |
| 2003/0142461 A1 | 7/2003 | Decker et al. |
| 2003/0219647 A1 | 11/2003 | Wariishi |
| 2003/0232153 A1 | 12/2003 | Nazarov et al. |
| 2004/0173873 A1 | 9/2004 | Kumar et al. |
| 2004/0222413 A1 | 11/2004 | Hsu et al. |
| 2005/0118083 A1 | 6/2005 | Tabuchi |
| 2005/0146671 A1 | 7/2005 | Khavrounyak et al. |
| 2006/0120014 A1 | 6/2006 | Nakamura et al. |
| 2006/0120020 A1 | 6/2006 | Dowgiallo |
| 2007/0001258 A1 | 1/2007 | Aihara |
| 2007/0108940 A1 | 5/2007 | Sainomoto et al. |
| 2007/0159767 A1 | 7/2007 | Jamison et al. |
| 2008/0002329 A1 | 1/2008 | Pohm et al. |
| 2008/0150484 A1 | 6/2008 | Kimball et al. |
| 2008/0266750 A1 | 10/2008 | Wu et al. |
| 2008/0283283 A1 | 11/2008 | Abe et al. |
| 2009/0034073 A1 | 2/2009 | Lazarev |
| 2009/0040685 A1 | 2/2009 | Hiemer et al. |
| 2009/0184355 A1 | 7/2009 | Brederlow et al. |
| 2009/0191394 A1 | 7/2009 | Lazarev et al. |
| 2010/0038629 A1 | 2/2010 | Lazarev |
| 2010/0085521 A1 | 4/2010 | Kasianova et al. |
| 2010/0178728 A1 | 7/2010 | Zheng et al. |
| 2010/0183919 A1 | 7/2010 | Holme et al. |
| 2010/0190015 A1 | 7/2010 | Kasianova |
| 2010/0193777 A1 | 8/2010 | Takahashi et al. |
| 2010/0214719 A1 | 8/2010 | Kim et al. |
| 2010/0233491 A1 | 9/2010 | Nokel et al. |
| 2010/0255381 A1 | 10/2010 | Holme et al. |
| 2010/0269731 A1 | 10/2010 | Jespersen et al. |
| 2010/0279122 A1 | 11/2010 | Nokel et al. |
| 2010/0309696 A1 | 12/2010 | Guillot et al. |
| 2010/0315043 A1 | 12/2010 | Chau |
| 2011/0006393 A1 | 1/2011 | Cui |
| 2011/0042649 A1 | 2/2011 | Duvall et al. |
| 2011/0064892 A1 | 3/2011 | Nokel et al. |
| 2011/0079733 A1 | 4/2011 | Langhals et al. |
| 2011/0079773 A1 | 4/2011 | Wasielewski et al. |
| 2011/0110015 A1 | 5/2011 | Zhang et al. |
| 2011/0228442 A1 | 9/2011 | Zhang et al. |
| 2012/0008251 A1 | 1/2012 | Yu et al. |
| 2012/0033342 A1 | 2/2012 | Ito et al. |
| 2012/0053288 A1 | 3/2012 | Morishita et al. |
| 2012/0056600 A1 | 3/2012 | Nevin |
| 2012/0113380 A1 | 5/2012 | Geivandov et al. |
| 2012/0244330 A1 | 9/2012 | Sun et al. |
| 2012/0268862 A1 | 10/2012 | Song et al. |
| 2012/0274145 A1 | 11/2012 | Taddeo |
| 2012/0302489 A1 | 11/2012 | Rodrigues et al. |
| 2013/0056720 A1 | 3/2013 | Kim et al. |
| 2013/0187475 A1 | 7/2013 | Vendik et al. |
| 2013/0194716 A1 | 8/2013 | Holme et al. |
| 2013/0215535 A1 | 8/2013 | Bellomo |
| 2013/0314839 A1 | 11/2013 | Terashima et al. |
| 2013/0342967 A1 | 12/2013 | Lai et al. |
| 2014/0035100 A1 | 2/2014 | Cho |
| 2014/0036410 A1 | 2/2014 | Okamatsu et al. |
| 2014/0098458 A1 | 4/2014 | Almadhoun et al. |
| 2014/0158340 A1 | 6/2014 | Dixler et al. |
| 2014/0185260 A1 | 7/2014 | Chen et al. |
| 2014/0268490 A1 | 9/2014 | Tsai et al. |
| 2014/0347787 A1 | 11/2014 | Fathi et al. |
| 2015/0008735 A1 | 1/2015 | Mizoguchi |
| 2015/0158392 A1 | 6/2015 | Zhao |
| 2015/0162131 A1 | 6/2015 | Felten et al. |
| 2015/0249401 A1 | 9/2015 | Eriksen et al. |
| 2015/0302990 A1 | 10/2015 | Ghosh et al. |
| 2016/0020026 A1 | 1/2016 | Lazarev |
| 2016/0020027 A1 | 1/2016 | Lazarev |
| 2016/0254092 A1 | 9/2016 | Lazarev et al. |
| 2016/0314901 A1 | 10/2016 | Lazarev |
| 2016/0340368 A1 | 11/2016 | Lazarev |
| 2016/0379757 A1 | 12/2016 | Robinson et al. |
| 2018/0137978 A1 | 5/2018 | Hein et al. |
| 2018/0137984 A1 | 5/2018 | Furuta et al. |

FOREIGN PATENT DOCUMENTS

| | | |
|---|---|---|
| CN | 203377785 U | 1/2014 |
| CN | 103986224 A | 8/2014 |
| DE | 10203918 A1 | 8/2003 |
| DE | 102010012949 A1 | 9/2011 |
| DE | 102011101304 A1 | 11/2012 |
| DE | 102012016438 A1 | 2/2014 |
| EP | 0493716 A1 | 7/1992 |
| EP | 0585999 A1 | 3/1994 |
| EP | 0602654 A1 | 6/1994 |
| EP | 0729056 A1 | 8/1996 |
| EP | 0791849 A1 | 8/1997 |
| EP | 1158320 A2 | 11/2001 |
| EP | 0986080 A3 | 1/2004 |
| EP | 0865142 B1 | 5/2008 |
| EP | 2062944 A1 | 5/2009 |
| EP | 2260035 A2 | 12/2010 |
| EP | 2415543 A1 | 2/2012 |
| EP | 1486590 B1 | 12/2013 |
| EP | 2759480 A1 | 7/2014 |
| GB | 547853 * | 9/1942 |
| GB | 923148 * | 4/1963 |
| GB | 2084585 B | 11/1983 |
| JP | S6386731 A | 4/1988 |
| JP | H03253014 A | 11/1991 |
| JP | 2786298 B2 | 8/1998 |
| JP | 2007287829 A | 11/2007 |
| JP | 2010106225 A | 5/2010 |
| JP | 2010160989 A | 7/2010 |
| JP | 2011029442 A | 2/2011 |
| JP | 2014139296 A | 7/2014 |
| RU | 2199450 C1 | 2/2003 |
| RU | 2512880 C2 | 4/2014 |
| WO | 1990009616 A1 | 8/1990 |
| WO | 0139305 A1 | 5/2001 |
| WO | 0226774 A2 | 4/2002 |
| WO | 2002094942 A9 | 4/2003 |
| WO | 2007078916 A2 | 7/2007 |
| WO | 2008038047 A2 | 4/2008 |
| WO | 2009158553 A2 | 12/2009 |
| WO | 2011056903 A1 | 5/2011 |

(56) References Cited

FOREIGN PATENT DOCUMENTS

| WO | 2012012672 A2 | 1/2012 |
|---|---|---|
| WO | 2012084536 A1 | 6/2012 |
| WO | 2012122312 A1 | 9/2012 |
| WO | 2012162500 A2 | 11/2012 |
| WO | 2013009772 A1 | 1/2013 |
| WO | 2013085467 A1 | 6/2013 |
| WO | 2014009686 A1 | 1/2014 |
| WO | 2015003725 A1 | 1/2015 |
| WO | 2015175522 A1 | 11/2015 |
| WO | 2015175558 A2 | 11/2015 |

OTHER PUBLICATIONS

Jaroslav Stejskal and Irina Sapurina, "Polyaniline: Thin Films and Colloidal Dispersions (IUPAC Technical Report)", Pure and Applied Chemistry, vol. 77, No. 5, pp. 815-826 (2005).
Notice of Allowance for U.S. Appl. No. 14/710,491, dated Oct. 24, 2016.
Roger D. Hartman and Herbert A. Pohl, "Hyper-electronic Polarization in Macromolecular Solids", Journal of Polymer Science: Part A-1, vol. 6, pp. 1135-1152 (1968).
Center for Dielectric Studies, Janosik, et al., "Ultra-High Energy Density Capacitors Through Improved Glass Technology", pp. 1-5 Center for Dielectric Studies Penn State University, dated 2004.
Congressional Research Service, Paul W. Parfomak, "Energy Storage for Power Grids and Electric Transportation: A Technology Assessment", pp. 87-94; Members and Committees of Congress; Mar. 27, 2012.
Department of Chemistry and Biochemistry, Hardy, et al. "Converting an Electrical Insulator into a Dielectric Capacitor: End-Capping Polystyrene with Oligoaniline"; pp. 799-807, Rensselaer Polytechnic Institute, Troy, New York 12180; Feb. 17, 2013.
Department of Chemistry, Ho et al., "High dielectric constant polyanilinelpoly(acrylic acid) composites prepared by in situ polymerization", pp. 630-637; National Taiwan University, Taipei, Taiwan, ROC, Apr. 15, 2008.
Hindawi Publishing Corporation, Chavez-Castillo et al, "Third-Order Nonlinear Optical Behavior of Novel Polythiophene Derivatives Functionalized with Disperse Red 19 Chromophore", pp. 1-11, International Journal of Polymer Science vol. 2015, Article ID 219361, Mar. 12, 2015.
Hindawi Publishing Corporation, González-Espasandin et al., "Fuel Cells: A Real Option for Unmanned Aerial Vehicles Propulsion", pp. 1-13, Torrej'on de Ardoz, 28850 Madrid, Spain Jan. 30, 2014.
Hindawi Punlishing Corporation, Khalil Ahmed et al., "High dielectric constant polyaniline/poly(acrylic acid) composites prepared by in situ polymerization", pp. 630-634, University of the Punjab, New Campus, Lahore 54590, Oct. 17, 2015.
Institute of Transportation Studies, Burke, et al., "Review of the Present and Future Applications of Supercapacitors in Electric and Hybrid Vehivles", pp. 2-23 UC Davis ITS; Dec. 2014.
International Search Report and Written Opinion for International Application No. PCT/US2015/058890, dated Feb. 25, 2016.
International Search Report and Written Opinion for International Application No. PCT/US2015/030356, dated Jul. 28, 2015.
International Search Report and Written Opinion for International Application No. PCT/US2015/030415, dated Nov. 4, 2015.
International Union of Pure and Applied Chemistry Polymer Divison Stejskal et al., "Polyaniline: Thin Films and colloidal Dispersions (IUPAC Technical Report)", vol. 77, No. 5, pp. 815-826, Russian Academy of Sciences, St. Petersburg 199004, Russia; 2005.
JACS Articles, Kang et. al., "Ultralarge Hyperpolarizability Twisted π-Electron System Electro-Optic Chromophores: Synthesis, Solid-State and Solution-Phase Structural Characteristics, Electronic Structures, Linear and Nonlinear optical Properties, and Computational Studies", pp. 3267-3286; Perugia, Italy Feb. 20, 2007.
Yue Wang, et. al., "Morphological and Dimensional Control via Hierarchical Assembly of Doped Oligoaniline Single Crystals", J. Am. Chem. Soc. 2012, 134, pp. 9251-9262.

Microelectronics Research and Communications Institute, Founders et al., "High-Voltage Switching Circuit for Nanometer Scale CMOS Technologies", pp. 1-4, University of Idaho, Moscow, ID 83843 USA, Apr. 30, 2007.
Molecular Diversity Preservation International, Barber, et al. "Polymer Composite and Nanocomposite Dielectric Materials for Pulse Power Energy Storage" pp. 1-32; 29 University of South Carolina, Columbia, SC 29208 Oct. 2009.
Optical Society of America, Kuzyk et al, "Theory of Molecular Nonlinear Optics", pp. 5, 4-82, Department of Physics and Astronomy, Washington State University, Pullman, Washington 99164-2814, USA, Mar. 26, 2013.
Philosophical Transactions of the Royal Society, SIMON, "Charge storage mechanism in nanoporous carbons and its consequence for electrical dounle layer capacitors" pp. 3457-3467; Drexel University, Philadelphia, PA 19104, 2010.
R. J. Baker and B. P. Johnson, "stacking power MOSFETs for use in high speed instrumentation", Department of Electrical Engineering, University of Nevada, Reno, Reno. Nevada 89557-0030; pp. 5799-5801 Aug. 3, 1992.
RSC Publishing, Akl et al., "Molecular materials for switchable nonlinear optics in the solid state, based on ruthenium-nitrosyl complexes", pp. 3518-3527, Porto Alegre, Brazil; May 24, 2013.
U.S. Appl. No. 15/053,943, to Pavel Ivan Lazarev, et al., filed Mar. 14, 2016.
U.S. Appl. No. 15/090,509, to Pavel Ivan Lazarev, et al., filed Mar. 4, 2016.
U.S. Appl. No. 14/752,600, to Matthew R. Robinson, et al., filed Jun. 26, 2015.
U.S. Appl. No. 14/919,337, to Paul T. Furuta, et al., filed Oct. 21, 2015.
U.S. Appl. No. 14/931,757, to Pavel Ivan Lazarev, et al., filed Nov. 3, 2015.
U.S. Appl. No. 15/043,186, to Paul T. Furuta, et al., filed Feb. 12, 2016.
U.S. Appl. No. 15/043,209, to Paul T. Furuta, et al., filed Feb. 12, 2016.
U.S. Appl. No. 15/043,247, to Barry K Sharp, et al., filed Feb. 12, 2016.
U.S. Appl. No. 14/719,072, to Pavel Ivan Lazarev, filed May 21, 2015.
U.S. Appl. No. 15/043,315, to Ivan S.G. Kelley-Morgan, filed Feb. 12, 2016.
U.S. Appl. No. 62/318,134, to Pavel Ivan Lazarev, et al., filed Mar. 4, 2016.
U.S. Appl. No. 62/294,964, to Pavel Ivan Lazarev, et al., filed Feb. 12, 2016.
U.S. Appl. No. 62/121,328, to Pavel Ivan Lazarev et al., filed Feb. 26, 2015.
U.S. Appl. No. 62/294,949, to Pavel Ivan Lazarev, et al., filed Feb. 12, 2016.
U.S. Appl. No. 62/294,955, to Pavel Ivan Lazarev, et al., filed Feb. 12, 2016.
International Search Report and Written Opinion dated Feb. 25, 2016 for International Application No. PCT/US15/58890, to Pavel Ivan Lazarev, filed Nov. 3, 2015.
International Search Report and Written Opinion dated Jul. 12, 2016 for International Application No. PCT/US2016/019641, to Pavel Ivan Lazarev, filed Feb. 25, 2016.
International Search Report and Written Opinion dated Sep. 1, 2016 for International Application No. PCT/US2016/033628, to Pavel Ivan Lazarev, filed Sep. 1, 2016.
International Search Report and Written Opinion dated Oct. 20, 2016 for International Application No. PCT/US2016/039395, to Matthew R. Robinson, et al., filed Jun. 24, 2016.
Non-Final Office Action for U.S. Appl. No. 14/752,600, dated Jan. 23, 2017.
Final Office Action for U.S. Appl. No. 15/043,247, dated Oct. 4, 2017.
Handy, Scott T. "Ionic Liquids-Classes and Properties" Published Sep. 2011, Accessed Aug. 28, 2017, InTechweb.org.
International Search Report and Written Opinion for International Application No. PCT/US2017/016862, dated Aug. 14, 2017.

(56) References Cited

OTHER PUBLICATIONS

International Search Report and Written Opinion for International Application No. PCT/US2017/24371, dated Aug. 2, 2017.
International Search Report and Written Opinion for International Application No. PCT/US2017/24600, dated Aug. 14, 2017.
Isoda, Kyosuke et al. "Truxene-Based Columnar Liquid Crystals: Self-Assembled Structures and Electro-Active Properties." Chemistry—An Asian Journal (2009), vol. 4, No. 10, pp. 1619-1625.
Johnson, Kieth E. "What's an Ionic Liquid?" The Electrochemical Society Interface, Published Spring 2007, pp. 38-41, Accessed Aug. 28, 2017.
Li, Li-Li et al. "Synthesis and Mesomorphism of Ether-ester Mixed Tail C3-symmetrical Truxene discotic liquid crystals." Liquid Crystals(2010), vol. 37, No. 5, pp. 499-506.
Liang, Mao et al. "Synthesis and Photovoltaic Performance of Two Triarylamine Organic Dyes Based on Truxene." Yinyong Huaxue (2011) vol. 28 No. 12, pp. 1387-1392.
Lu, Meng et al. "Organic Dyes Incorporating Bis-hexapropyltruxeneamino Moiety for efficient Dye-sensitized Solar Cells." Journal of Physical Chemistry C (2011) vol. 115, No. 1, pp. 274-281.
Maddalena, Francesco "Why are Ionic Liquids, Liquids?" http://www.quora.com/why-are-ionic-liquids-liquids?, Published Jan. 26, 2017, Accessed Aug. 28, 2017.
Nagabrahmandachari et al. "Synthesis and Spectral Analysis of Tin Tetracarboxylates and Phosphinates" Indian Journal of Chemistry—Section A, 1995, vol. 34A, pp. 658-660.
Ni, Hai-Lang et al. "Truxene Discotic Liquid Crystals with Two Different Ring Substituents: Synthesis, Metamorphosis and High Charged Carrier Mobility." Liquid Crystals, vol. 40, No. 3, pp. 411-420.
Non-Final Office Action for U.S. Appl. No. 14/719,072, dated Aug. 2, 2017.
Non-Final Office Action for U.S. Appl. No. 15/043,247, dated Jun. 22, 2017.
Non-Final Office Action for U.S. Appl. No. 15/194,224, dated Sep. 27, 2017.
Notice of Allowance for U.S. Appl. No. 14/710,480, dated Oct. 6, 2017.
Notice of Allowance for U.S. Appl. No. 14/752,600, dated Jul. 27, 2017.
Notice of Allowance for U.S. Appl. No. 15/053,943, dated Aug. 14, 2017.
Trevethan, Thomas et al. "Organic Molecules Reconstruct Nanostructures on Ionic Surfaces." Small (2011), vol. 7, No. 9, pp. 1264-1270.
Warmerdam, T. W. et al. "Discotic Liquid Crystals. Physical Parameters of some 2, 3, 7, 8, 12, 13-hexa(alkanoyloxy) truxenes: Observation of a Reentrant Isotropic Phase in a Pure Disk-like mesogen." Liquid Crystals (1988), vol. 3, No. 8, pp. 1087-1104.
Deily, Dielectric and Optical Characterization of Polar Polymeric Materials: Chromophore Entrained PMMA Thin Films, Thesis, 2008.
Deruiter, J. Resonance and Induction Tutorial. Auburn University-Principles of Drug Action 1 Course Material. Spring 2005, 19 pages.
International Search Report and Written Opinion for International Application No. PCT/US2016/57765, dated Jan. 5, 2017.
International Search Report and Written Opinion for International Application No. PCT/US2017/017146, dated May 11, 2017.
International Search Report and Written Opinion for International Application No. PCT/US2017/017150, dated May 18, 2017.
International Search Report and Written Opinion for International Application No. PCT/US2017/24150, dated Jun. 21, 2017.
Manukian, BK. 216. IR.-spektroskopische Untersuchungen in der Imidazol-Reihe. Helvetica Chimica Acta. 1965, vol. 48, p. 2001.
Non-Final Office Action dated Jun. 13, 2017 for U.S. Appl. 15/163,595.
Non-Final Office Action for U.S. Appl. No. 15/053,943, dated Apr. 19, 2017.
Non-Final Office Action for U.S. Appl. No. 14/710,480, dated May 8, 2017.
Non-Final Office Action for U.S. Appl. No. 15/043,186, dated Jun. 2, 2017.
Non-Final/Final Office Action for U.S. Appl. No. 15/043,247, dated Jun. 22, 2017.
Notice of Allowance for U.S. Appl. No. 14/710,491, dated Jan. 19, 2017.
Notice of Allowance for U.S. Appl. No. 14/931,757, dated Jul. 17, 2017.
Extended European Search Report for Application No. 15792405.1, dated Nov. 10, 2017.
Hsing-Yang Tsai et al, "1,6- and 1,7-Regioisomers of Asymmetric and Symmetric Perylene Bisimides: Synthesis, Characterization and Optical Properties" Molecules, 2014, vol. 19, pp. 327-341.
Hsing-Yang Tsai et al, "Synthesis and optical properties of novel asymmetric perylene bisimides", Journal of Luminescence, Vole 149, pp. 103-111 (2014).
Notice of Allowance for U.S. Appl. No. 14/710,480, dated Nov. 24, 2017.
Notice of Allowance for U.S. Appl. No. 14/719,072, dated Nov. 16, 2017.
Notice of Allowance for U.S. Appl. No. 14/931,757, dated Oct. 31, 2017.
Office Action dated Oct. 19, 2017 for Taiwan patent Application No. 106104501.
D C Tiwari, et al: "Temperature dependent studies of electric and dielectric properties of polythiophene based nano composite", Indian Journal of Pure & Applied PhysicsVol. 50, Jan. 2012. pp. 49-56.
Extended European Search Report. 15792494.5, dated Dec. 11, 2017.
Non-Final Office Action for U.S. Appl. No. 15/043,315, dated Dec. 26 2017.
Notice of Allowance for U.S. Appl. No. 14/751,600, dated Nov. 24, 2017.
Notice of Allowance for U.S. Appl. No. 14/751,600, dated Dec. 4, 2017.
Notice of Allowance for U.S. Appl. No. 14/931,357, dated Dec. 29, 2017.
Office Action dated Dec. 13, 2017 for Taiwan Patent Application No. 106104499.
Office Action dated Dec. 13, 2017 for Taiwan Patent Application No. 106104500.
Final Office Action for U.S. Appl. No. 15/043,249, dated Feb. 6, 2018.
Final Office Action for U.S. Appl. No. 15/194,224, dated Jan. 30, 2018.
Non-Final Office Action for U.S. Appl. No. 15/163,595, dated Jan. 17, 2018.
Notice of Allowance for U.S. Appl. No. 15/090,509, dated Jan. 24, 2018.
Notice of Allowance for U.S. Appl. No. 14/710,480, dated Jan. 11, 2018.
Updated Notice of Allowance for U.S. Appl. No. 14/710,480, dated Jan. 17, 2018.
Non-Final Office Action for U.S. Appl. No. 15/090,509, dated Jun. 22, 2017.
Non-Final Office Action for U.S. Appl. No. 15/449,587, dated May 21, 2018.
Non-Final Office Action for U.S. Appl. No. 15/805,016, dated Jun. 4, 2018.

\* cited by examiner

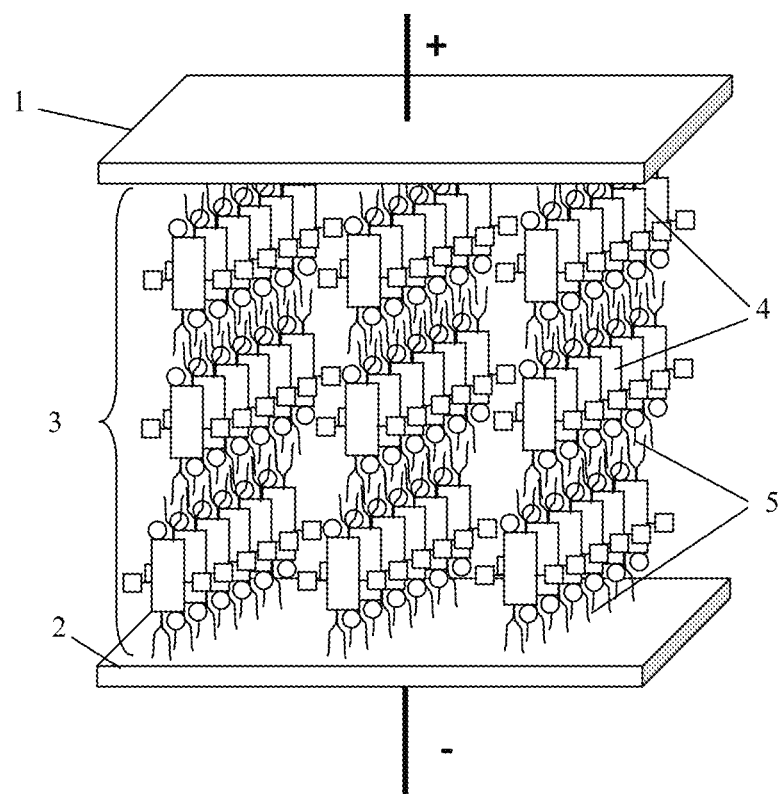

ORGANIC COMPOUND, CRYSTAL DIELECTRIC LAYER AND CAPACITOR

BACKGROUND

A capacitor is a passive electronic component that is used to store energy in the form of an electrostatic field, and comprises a pair of electrodes separated by a dielectric layer. Each of the electrodes has an area A and are separated from each other by a distance d. When a potential difference exists between two electrodes, an electric field is present in the dielectric layer. This field stores energy and an ideal capacitor is characterized by a single constant value of capacitance which is the ratio of the electric charge on each electrode to the potential difference between them. Charge may be considered to be distributed uniformly over the area A of each electrode, and a surface charge density σ for each electrode can be expressed as $\pm\sigma=\pm Q/A$. As the width of the electrodes is much greater than the separation (distance) d, an electrical field near the center of the capacitor will be uniform with the magnitude $E=\rho/\in$. Voltage is defined as a line integral of the electric field between electrodes. An ideal capacitor is characterized by a constant capacitance C, defined by the formula (1)

$$C=Q/V, \qquad (1)$$

which shows that capacitance increases with area and decreases with distance. For high voltage applications much larger capacitors have to be used.

One of important characteristic of a dielectric material is its breakdown voltage $V_{bd}$. There are a number of factors that can dramatically reduce the breakdown voltage that is a breakdown of dielectric layer along electric field lines will take place. Geometry of the conductive electrodes is important for these applications. In particular, sharp edges or points hugely increase the electric field strength locally and can lead to a local breakdown. Once a local breakdown starts at any point, the breakdown will quickly "trace" through the dielectric layer till it reaches the opposite electrode and causes a short circuit.

Breakdown of the dielectric layer usually occurs as follows. Intensity of an electric field becomes high enough to "pull" electrons from atoms of the dielectric material and make them conduct an electric current from one electrode to another. Presence of impurities in the dielectric or imperfections of the crystal structure can result in an avalanche breakdown as observed in semiconductor devices.

A characteristic electric field known as the breakdown strength $E_{bd}$, is the electric field intensity at which the dielectric layer in a capacitor becomes conductive. The breakdown voltage is related to the breakdown strength by the product of dielectric strength and separation between the electrodes, $$V_{bd}=E_{bd}d \qquad (2)$$

Another of important characteristic of a dielectric material is its dielectric permittivity $\in$. Different types of dielectric materials are used for capacitors and include ceramics, polymer film, paper, and electrolytic capacitors of different kinds. The most widely used polymer film materials are polypropylene and polyester. Increase of dielectric permittivity allows increasing of volumetric energy density which makes it an important technical task. The dielectric permittivity $\in$ for a material is often expressed as the product of a dimensionless dielectric constant κ and the permittivity of free space $\in_0$ (8.85×10$^{-12}$ Farads/meter). Therefore the capacitance is largest in devices made of materials of high permittivity.

The maximal volumetric energy density stored in the capacitor is proportional to $\sim\in\cdot E^2_{bd}$. Thus, in order to increase the stored energy of the capacitor it is necessary to increase dielectric permittivity $\in$ (or dielectric constant κ) and breakdown strength $E_{bd}$ of the dielectric material.

An ultra-high dielectric constant composite of polyaniline, PANI-DBSA/PAA, was synthesized using in situ polymerization of aniline in an aqueous dispersion of polyacrylic acid (PAA) in the presence of dodecylbenzene sulfonate (DBSA) (see, Chao-Hsien Hoa et al., "High dielectric constant polyaniline/poly(acrylic acid) composites prepared by in situ polymerization", Synthetic Metals 158 (2008), pp. 630-637). The water-soluble PAA served as a polymeric stabilizer, protecting the PANI particles from macroscopic aggregation. A very high dielectric constant of ca. 2.0*10$^5$ (at 1 kHz) was obtained for the composite containing 30% PANI by weight. Influence of the PANI content on the morphological, dielectric and electrical properties of the composites was investigated. Frequency dependence of dielectric permittivity, dielectric loss, loss tangent and electric modulus were analyzed in the frequency range from 0.5 kHz to 10 MHz. SEM micrograph revealed that composites with high PANI content (i.e., 20 wt. %) consisted of numerous nano-scale PANI particles that were evenly distributed within the PAA matrix. High dielectric constants were attributed to the sum of the small capacitors of the PANI particles. The drawback of this material is a possible occurrence of percolation and formation of at least one continuous electrically conductive channel under electric field with probability of such an event increasing with an increase of the electric field. When at least one continuous electrically conductive channel (track) through the neighboring conducting PANI particles is formed between electrodes of the capacitor, it decreases a breakdown voltage of such capacitor.

Colloidal polyaniline particles stabilized with a water-soluble polymer, poly(N-vinylpyrrolidone) [poly(1-vinylpyrrolidin-2-one)], have been prepared by dispersion polymerization. The average particle size, 241±50 nm, have been determined by dynamic light scattering (see, Jaroslav Stejskal and Irina Sapurina, "Polyaniline: Thin Films and Colloidal Dispersions (IUPAC Technical Report)", Pure and Applied Chemistry, Vol. 77, No. 5, pp. 815-826 (2005).

Single crystals of doped aniline oligomers are produced via a simple solution-based self-assembly method (see, Yue Wang, et. al., "Morphological and Dimensional Control via Hierarchical Assembly of Doped Oligoaniline Single Crystals", J. Am. Chem. Soc. 2012, 134, pp. 9251-9262). Detailed mechanistic studies reveal that crystals of different morphologies and dimensions can be produced by a "bottom-up" hierarchical assembly where structures such as one-dimensional (1-D) nanofibers can be aggregated into higher order architectures. A large variety of crystalline nanostructures, including 1-D nanofibers and nanowires, 2-D nanoribbons and nanosheets, 3-D nanoplates, stacked sheets, nanoflowers, porous networks, hollow spheres, and twisted coils, can be obtained by controlling the nucleation of the crystals and the non-covalent interactions between the doped oligomers. These nanoscale crystals exhibit enhanced conductivity compared to their bulk counterparts as well as interesting structure-property relationships such as shape-dependent crystallinity. Furthermore, the morphology and dimension of these structures can be largely rationalized and predicted by monitoring molecule-solvent interactions via absorption studies. Using doped tetra-aniline as a model system, the results and strategies presented in this article provide insight into the general scheme of shape and size control for organic materials.

Thus, materials with high dielectric permittivity which are based on composite materials and containing polarized particles (such as PANI particles) may demonstrate a percolation phenomenon. The formed polycrystalline structure of layers has multiple tangling chemical bonds on borders between crystallites. When the used material with high dielectric permittivity possesses polycrystalline structure, a percolation may occur along the borders of crystal grains.

Hyper-electronic polarization of organic compounds is described in greater detail in Roger D. Hartman and Herbert A. Pohl, "Hyper-electronic Polarization in Macromolecular Solids", Journal of Polymer Science: Part A-1 Vol. 6, pp. 1135-1152 (1968). Hyper-electronic polarization may be viewed as the electrical polarization external fields due to the pliant interaction with the charge pairs of excitons, in which the charges are molecularly separated and range over molecularly limited domains. In this article four polyacene quinone radical polymers were investigated. These polymers at 100 Hz had dielectric constants of 1800-2400, decreasing to about 58-100 at 100,000 Hz. An essential drawback of the described method of production of material is use of a high pressure (up to 20 kbars) for forming the samples intended for measurement of dielectric constants.

Capacitors as energy storage device have well-known advantages versus electrochemical energy storage, e.g. a battery. Compared to batteries, capacitors are able to store energy with very high power density, i.e., very high charge/recharge rates, have long shelf life with little degradation, and can be charged and discharged (cycled) hundreds of thousands or millions of times. However, conventional capacitors often do not store energy in a sufficiently small volume or weight as compared to the case of a battery, or at low energy storage cost, which makes capacitors impractical for some applications, for example electric vehicles. Accordingly, it may be an advance in energy storage technology to provide capacitors of higher volumetric and mass energy storage density and lower cost.

SUMMARY

The present disclosure provides an organic compound characterized by electronic polarizability and having a following general structural formula:

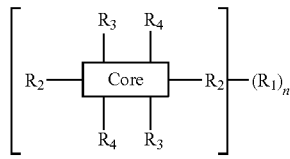

where Core is an aromatic polycyclic conjugated molecule, $R_1$ is group providing solubility of the organic compound in an organic solvent, n is 1, 2, 3, 4, 5, 6, 7 or 8, $R_2$ is substitute located in apex positions, R3 and R4 are substitutes located in side (lateral) positions and, the core has flat anisometric form and the $R_2$ substitutes are selected from hydrogen and electrophilic groups (acceptors) and $R_3$ substitutes and $R_4$ substitutes are independently selected from hydrogen and nucleophilic groups (donors) or vice versa $R_3$ substitutes and $R_4$ substitutes are independently selected from hydrogen and nucleophilic groups (donors) and $R_2$ substitutes are selected from hydrogen and electrophilic groups (acceptors), and the substitutes $R_2$, $R_3$ and $R_4$ cannot be hydrogen simultaneously.

In an aspect, the present disclosure provides a crystal dielectric layer comprising the disclosed organic compound.

In another aspect, the present disclosure provides a capacitor comprising a first electrode, a second electrode, and a crystal dielectric layer disposed between said first and second electrodes, wherein said electrodes are flat and planar and positioned parallel to each other, and wherein said crystal dielectric layer comprises the disclosed organic compound. Said crystal dielectric layer comprises supramolecules formed with the aromatic polycyclic conjugated cores, and isotropic insulating sublayers formed with the substitutes served as the isolating groups Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWING

FIG. 1 schematically shows a capacitor according to an aspect of the present disclosure.

DETAILED DESCRIPTION

While various implementations of aspects of the present disclosure have been shown and described herein, it will be obvious to those skilled in the art that such implementations are provided by way of example only. Numerous variations, changes, and substitutions may occur to those skilled in the art without departing from the aspects of the present disclosure. It should be understood that various alternatives to the implementations described herein may be employed.

The present disclosure provides an organic compound. Existence of the electrophilic groups (acceptors) and the nucleophilic groups (donors) in the aromatic polycyclic conjugated core promotes increase of electronic polarizability of these cores. Under the influence of an external electric field electrons are displaced from the nucleophilic groups (donors) to the electrophilic groups (acceptors) that lead to increase of an electronic polarizability of such molecules. Thus a distribution of electronic density in the core is non-uniform.

In one implementation, the $R_1$ groups serve as the isolating groups and are attached to the aromatic polycyclic conjugated core in apex positions and/or side position. In another embodiment of the present invention, the aromatic polycyclic conjugated Core in the above general structural formula comprises rylene fragments. In still another embodiment of the present invention, the rylene fragments are selected from structures 1-21 as given in Table 1.

TABLE 1
Examples of the polycyclic organic compound comprising rylene fragments
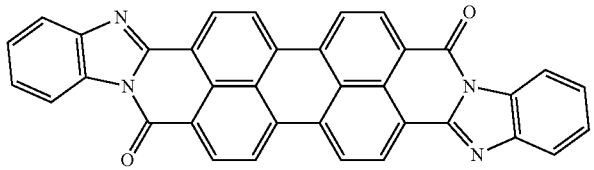 [SMILES: O=c1c2ccc3c4ccc5c6c(ccc(c7ccc(c2c37)c2nc3ccccc3n12)c46)c(=O)n1c2ccccc2nc51]
1
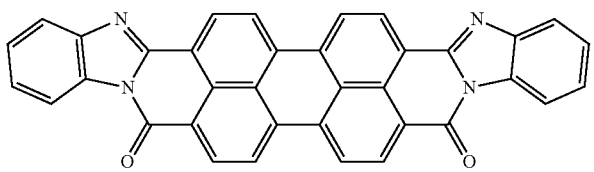 [SMILES: O=c1c2ccc3c4ccc5c(=O)n6c7ccccc7nc6c6ccc(c7ccc(c2c37)c2nc3ccccc3n12)c4c56]
2
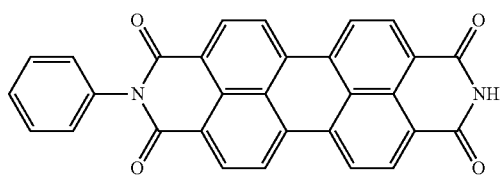 [SMILES: O=C1NC(=O)c2ccc3c4ccc5c6c(ccc(c7ccc1c2c73)c64)C(=O)N(c1ccccc1)C5=O]
3
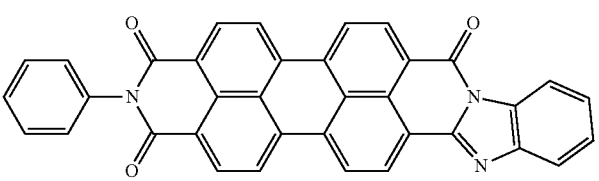 [SMILES: O=C1c2ccc3c4ccc5c(=O)n6c7ccccc7nc6c6ccc(c7ccc(c2c37)C(=O)N1c1ccccc1)c4c56]
4
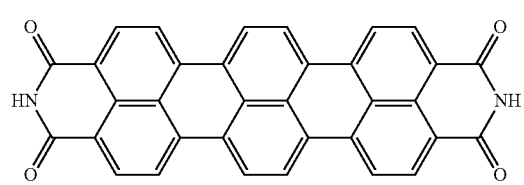 [SMILES: O=C1NC(=O)c2ccc3c4ccc5c6ccc7c8c(ccc(c9ccc(c%10ccc1c2c%103)c4c95)c86)C(=O)NC7=O]
5
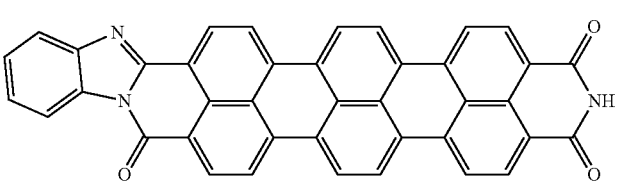 [SMILES: O=C1NC(=O)c2ccc3c4ccc5c6ccc7c8c(ccc(c9ccc(c%10ccc1c2c%103)c4c95)c68)c(=O)n1c2ccccc2nc71]
6
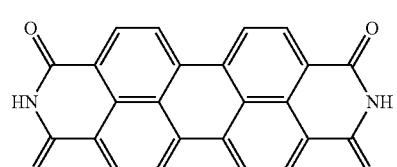
7
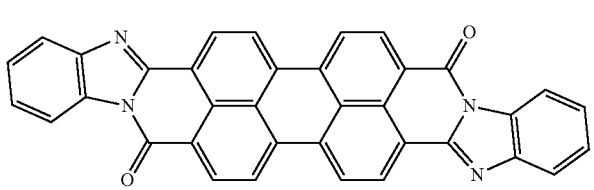 [SMILES: O=c1c2ccc3c4ccc5c6c(ccc(c7ccc(c2c37)c2nc3ccccc3n12)c46)c(=O)n1c2ccccc2nc51]
8

TABLE 1-continued
Examples of the polycyclic organic compound comprising rylene fragments
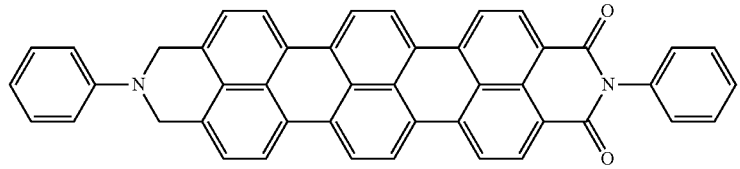 [SMILES: O=C1c2ccc3c4ccc5c6ccc7c8c(ccc(c9ccc(c%10ccc(c2c3%10)C(=O)N1c1ccccc1)c4c59)c86)CN(c1ccccc1)C7]
9
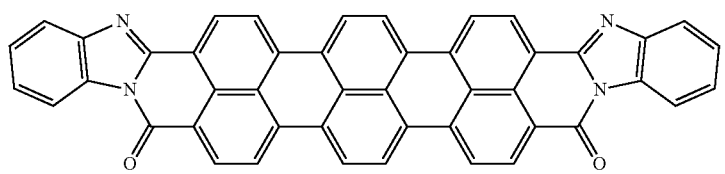 [SMILES: O=c1c2ccc3c4ccc5c6ccc7c(=O)n8c9ccccc9nc8c8ccc(c9ccc(c%10ccc(c2c3%10)c2nc3ccccc3n12)c4c59)c6c78]
10
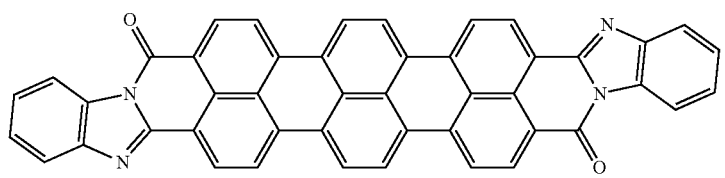 [SMILES: O=c1c2ccc3c4ccc5c6ccc7c8c(ccc(c9ccc(c%10ccc(c2c3%10)c2nc3ccccc3n12)c4c95)c68)c(=O)n1c2ccccc2nc71]
11
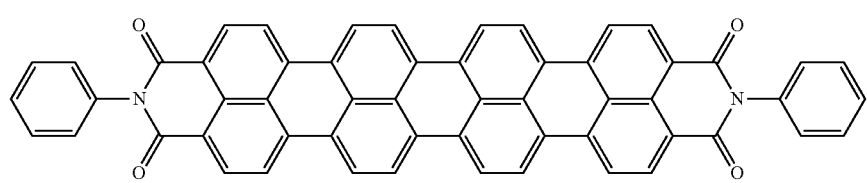 [SMILES: O=C1c2ccc3c4ccc5c6ccc7c8ccc9c%10c(ccc(c%11ccc(c%12ccc(c%13ccc(c2c3%13)C(=O)N1c1ccccc1)c4c5%12)c6c7%11)c%108)C(=O)N(c1ccccc1)C9=O]
12
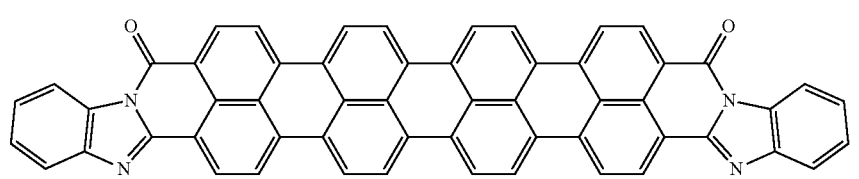 [SMILES: O=c1c2ccc3c4ccc5c6ccc7c8ccc9c(=O)n%10c%11ccccc%11nc%10c%10ccc(c%11ccc(c%12ccc(c%13ccc(c2c3%13)c2nc3ccccc3n12)c4c5%12)c6c7%11)c8c9%10]
13
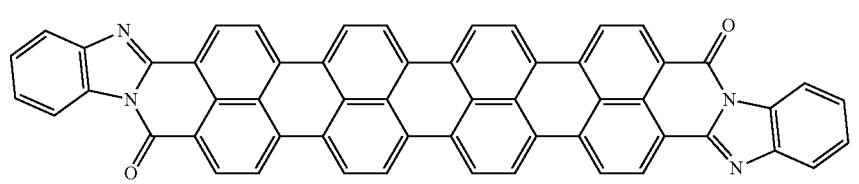 [SMILES: O=c1c2ccc3c4ccc5c6ccc7c8ccc9c%10c(ccc(c%11ccc(c%12ccc(c%13ccc(c2c3%13)c2nc3ccccc3n12)c4c5%12)c6c%117)c8%10)c(=O)n1c2ccccc2nc91]
14
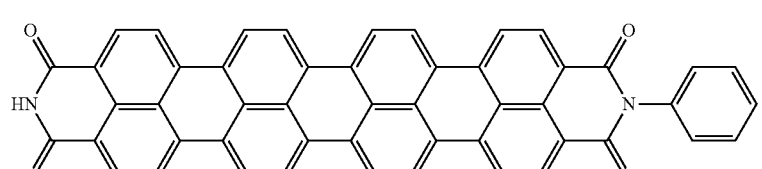
15
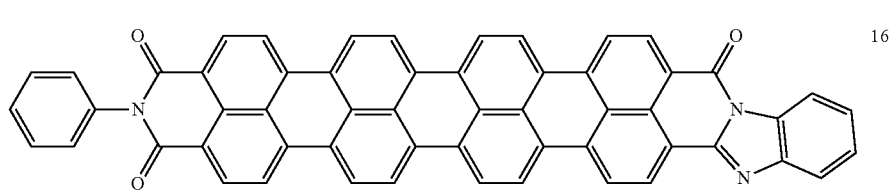
16

TABLE 1-continued

Examples of the polycyclic organic compound comprising rylene fragments

| | |
|---|---|
| [structure] | 17 |
| [structure] | 18 |
| [structure] | 19 |
| [structure] | 20 |
| [structure] | 21 |

In another implementation of the organic compound, the aromatic polycyclic conjugated Core in the above general structural formula comprises an electro-conductive oligomer including a phenylene oligomer and a polyacene quinine radical oligomer. In still another embodiment of the present invention, the electro-conductive oligomer is selected from the structures 22 to 30 as given in Table 2 wherein I=2, 3, 4, 5, 6, 7, 8, 9, 10, 11 or 12, Z is =O, =S or =NR$_1$, and R$_1$ is selected from the group consisting of unsubstituted or substituted C$_1$-C$_{18}$alkyl, unsubstituted or substituted C$_2$-C$_{18}$alkenyl, unsubstituted or substituted C$_2$-C$_{18}$alkynyl, and unsubstituted or substituted C$_4$-C$_{18}$aryl.

TABLE 2

Examples of the polycyclic organic compound comprising electro-conductive oligomer

| | |
|---|---|
| [structure] | 22 |

TABLE 2-continued

Examples of the polycyclic organic compound comprising electro-conductive oligomer

| | |
|---|---|
| [structure] | 23 |
| [structure] | 24 |
| [structure] | 25 |

TABLE 2-continued

Examples of the polycyclic organic compound comprising electro-conductive oligomer

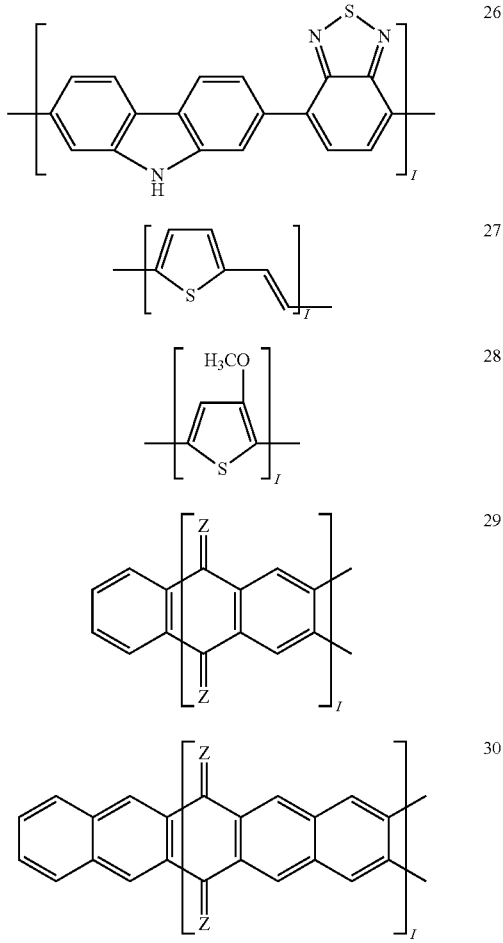

In yet another implementation, the aforementioned electrophilic groups (acceptors) in the above general structural formula are selected from —NO₂, —NH₃⁺ and —NR₃⁺ (quaternary nitrogen salts), counterion Cl⁻ or Br⁻, —CHO (aldehyde), —CRO (keto group), —SO₃H (sulfonic acids), —SO₃R (sulfonates), SO₂NH₂ (sulfonamides), —COOH (carboxylic acid), —COOR (esters, from carboxylic acid side), —COCl (carboxylic acid chlorides), —CONH₂ (amides, from carboxylic acid side), —CF₃, —CCl₃, —CN, wherein R is radical selected from the list comprising alkyl (methyl, ethyl, isopropyl, tert-butyl, neopentyl, cyclohexyl etc.), allyl (—CH₂—CH=CH₂), benzyl (—CH₂C₆H₅) groups, phenyl (+substituted phenyl) and other aryl (aromatic) groups.

In still another implementation, the aforementioned nucleophilic groups (donors) in the above general structural formula are selected from —O⁻(phenoxides, like —ONa or —OK), —NH₂, —NHR, NR₂, —OH, OR (ethers), —NH-COR (amides, from amine side), —OCOR (esters, from alcohol side), alkyls, —C₆H₅, vinyls, wherein R is radical selected from the list comprising alkyl (methyl, ethyl, isopropyl, tert-butyl, neopentyl, cyclohexyl etc.), allyl (—CH₂—CH=CH₂), benzyl (—CH₂C₆H₅) groups, phenyl (+substituted phenyl) and other aryl (aromatic) groups. In one implementation, the organic solvent is selected from benzene, toluene, xylenes, acetone, acetic acid, methylethylketone, hydrocarbons, chloroform, carbontetrachloride, methylenechloride, dichlorethane, chlorobenzene, alcohols, nitromethan, acetonitrile, dimethylforamide, 1,4-dioxane, tetrahydrofuran (THF), methylcyclohexane (MCH), and any combination thereof. In another implementation, the groups providing solubility of the organic compound are independently selected from alkyl, aryl, substituted alkyl, substituted aryl, fluorinated alkyl, chlorinated alkyl, branched and complex alkyl, branched and complex fluorinated alkyl, branched and complex chlorinated alkyl groups, and any combination thereof, and wherein the alkyl group is selected from methyl, ethyl, propyl, butyl, I-butyl and t-butyl groups, and the aryl group is selected from phenyl, benzyl and naphthyl groups.

In yet another implemenation, the aromatic polycyclic conjugated Core in the above general structural formula comprises rylene fragment, the amino groups (—NH₂) are used as donors, nitro groups are used as acceptors and said organic compound formulas are selected from structures 31 to 36 as shown in Table 3.

TABLE 3

Examples of the organic compound

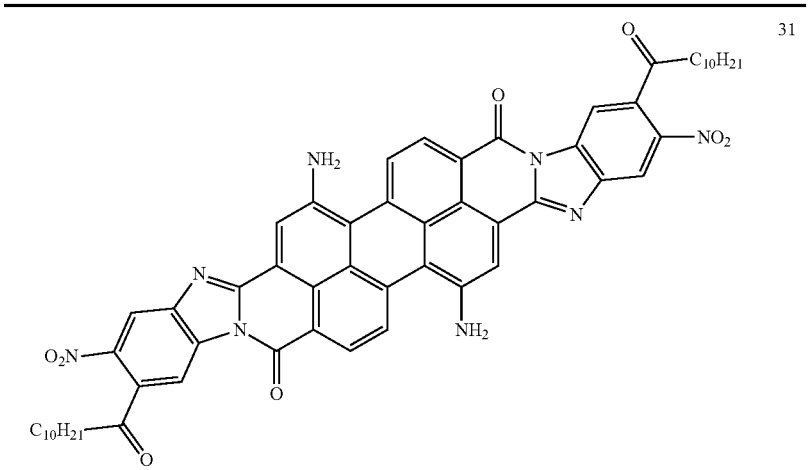

TABLE 3-continued
Examples of the organic compound
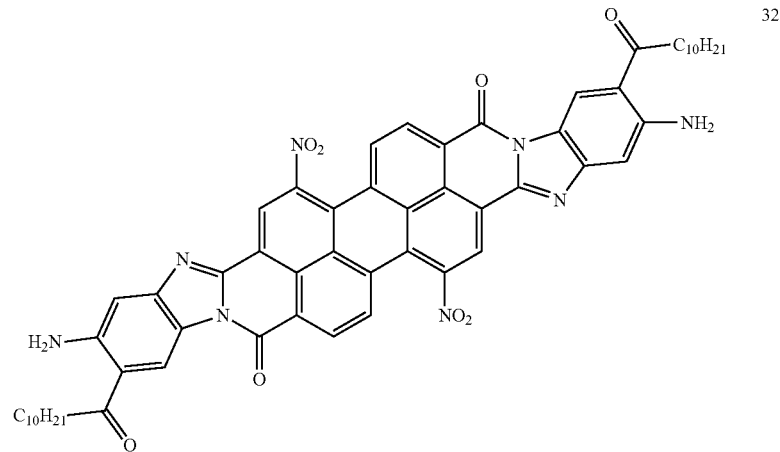
32
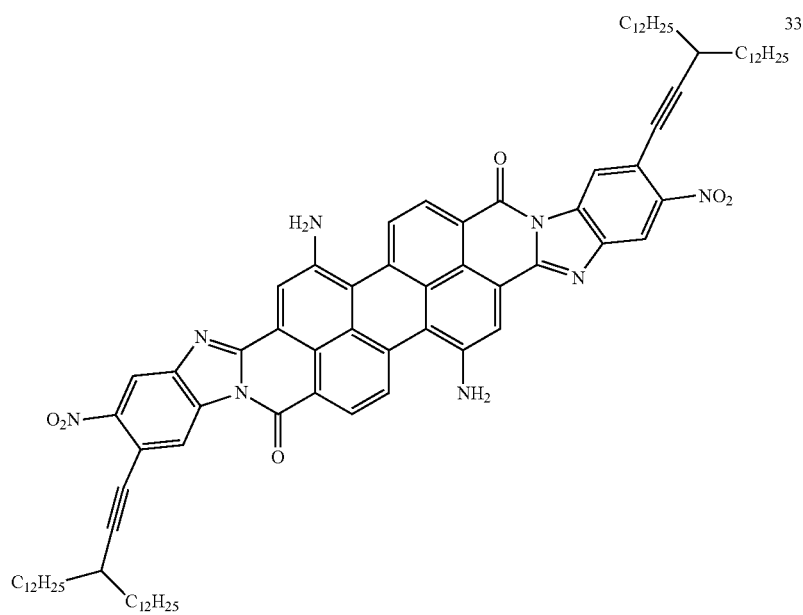
33

TABLE 3-continued
Examples of the organic compound
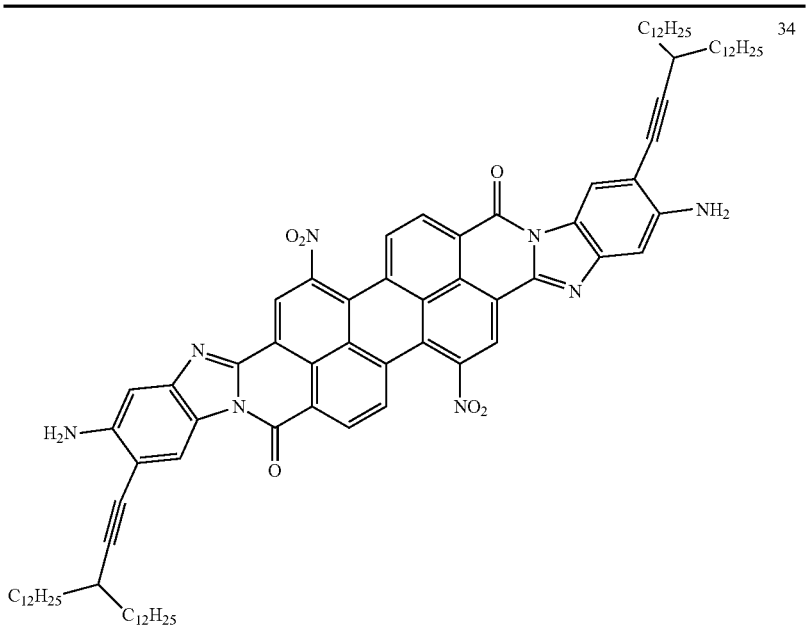
34
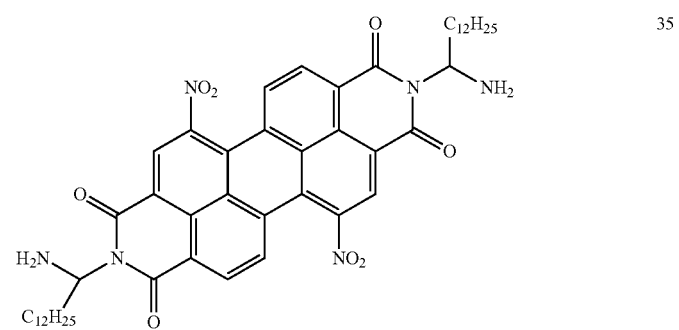
35
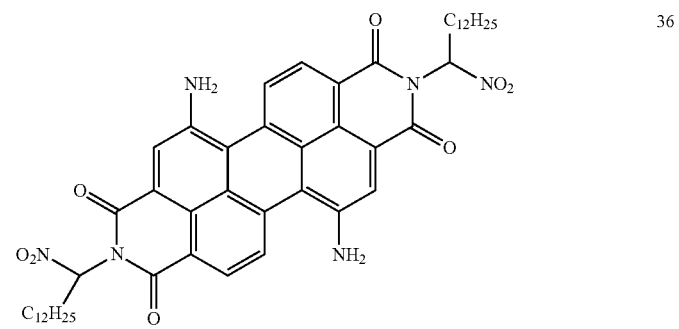
36

In yet another implementation, the aromatic polycyclic conjugated Core in the above general structural formula comprises rylene fragment and selected from structures 37-39 as shown in Table 4, where other ring position of $R_1$ and $R_2$ are possible so that trans and cis isomers are possible.

TABLE 4

Examples of the organic compound

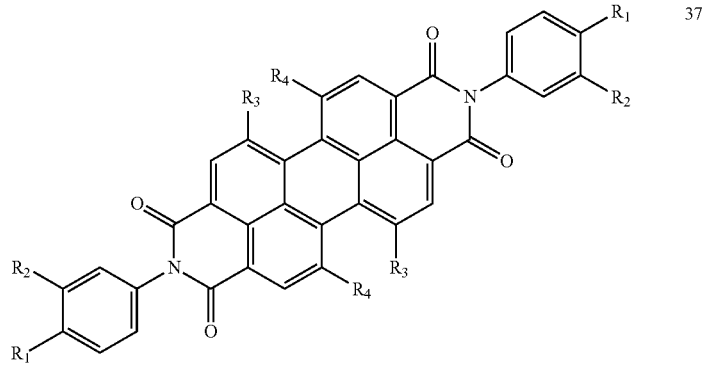

37

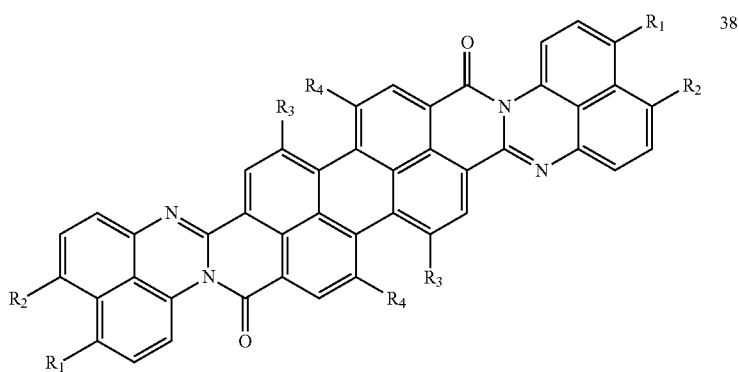

38

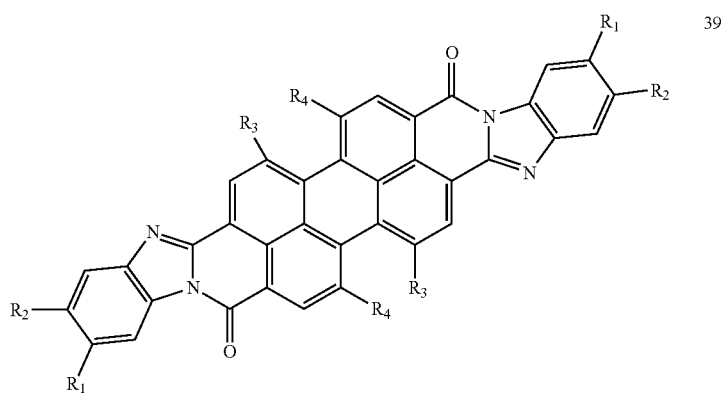

39

In still another embodiment of the present invention, the aromatic polycyclic conjugated Core in the above general structural formula comprises rylene fragment and has a structure selected from structures 40-43 as shown in Table 5.

TABLE 5
Examples of the organic compound
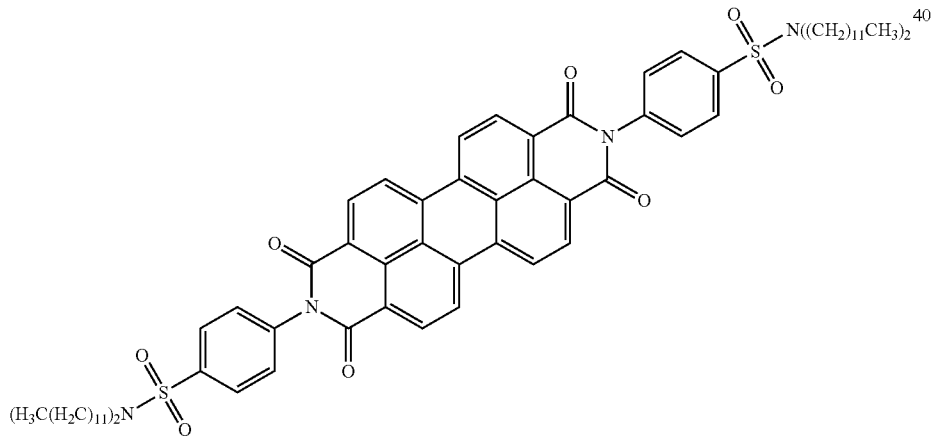
40
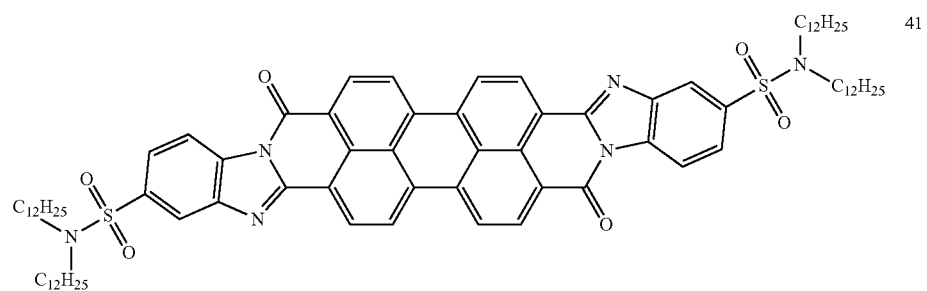
41
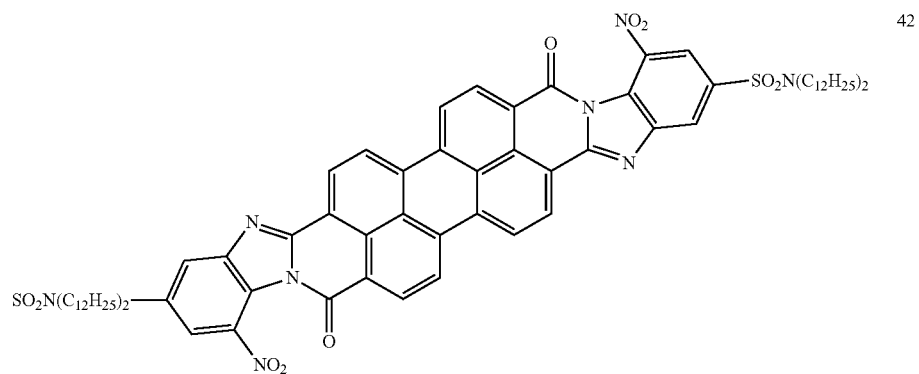
42
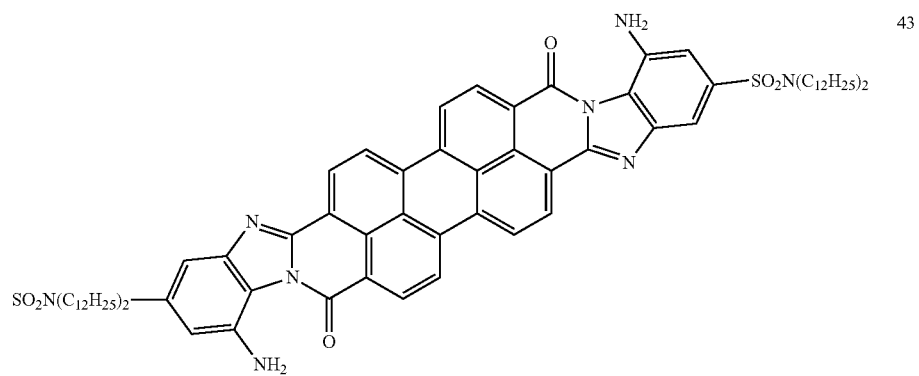
43

21 22
TABLE 5-continued
Examples of the organic compound
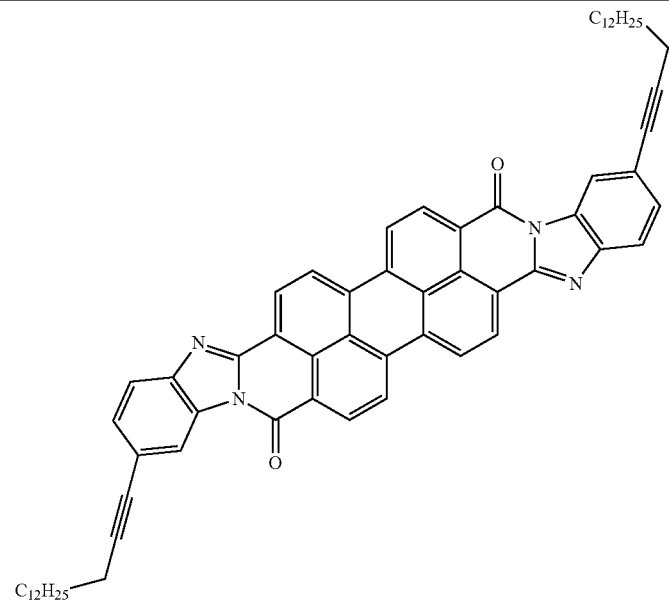
44
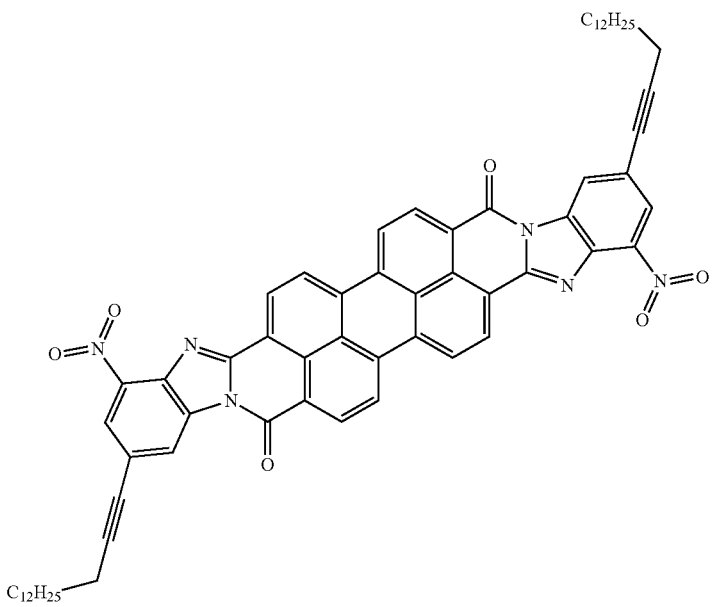
45

TABLE 5-continued

Examples of the organic compound

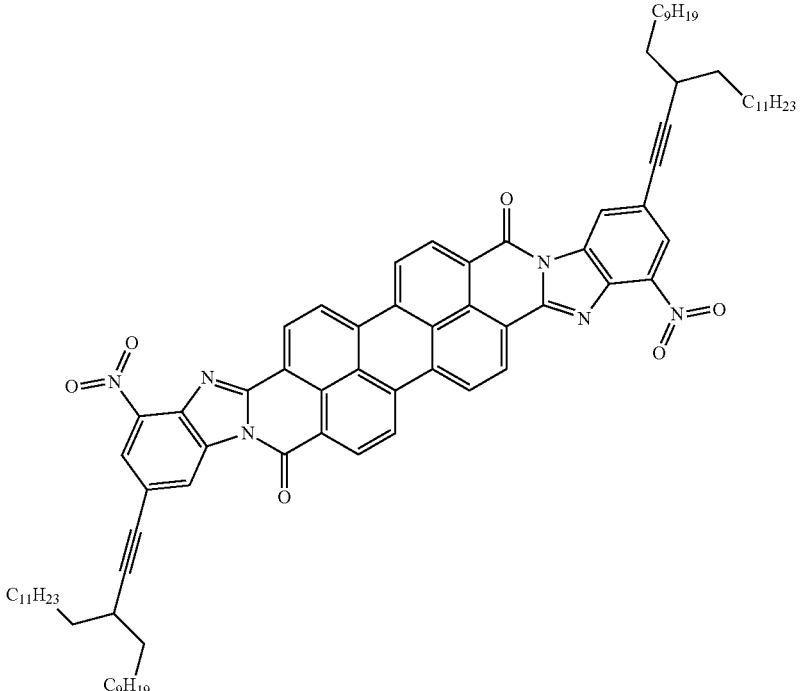

46

In an aspect, the present disclosure provides a crystal dielectric layer comprising the disclosed organic compound. The crystal dielectric layers are produced from the disclosed organic compound by Cascade Crystallization. The symmetric arrangement of electrophilic groups (acceptors) and nucleophilic groups (donors) in the aromatic polycyclic conjugated core promotes formation of supramolecules.

Cascade Crystallization process involves a chemical modification step and four steps of ordering during the crystal dielectric layer formation. The chemical modification step introduces hydrophilic groups on the periphery of the molecule of the disclosed organic compound in order to impart amphiphilic properties to the molecule. Amphiphilic molecules stack together into supramolecules, which is the first step of ordering. At certain concentration, supramolecules are converted into a liquid-crystalline state to form a lyotropic liquid crystal, which is the second step of ordering. The lyotropic liquid crystal is deposited under the action of a shear force (or meniscus force) onto a substrate based on a Mayer Rod shearing technique, so that shear force (or the meniscus) direction determines the crystal axis direction in the resulting solid crystal layer. The external alignment upon the lyotropic liquid crystal, can be produced using any other means, for example by applying an external electric field at normal or elevated temperature, with or without additional illumination, magnetic field, or optical field (e.g., coherent photovoltaic effect); the degree of the external alignment should be sufficient to impart necessary orientation to the supramolecules of the lyotropic liquid crystal and form a structure, which serves as a base of the crystal lattice of the crystal dielectric layer. This directional deposition is third step of ordering, representing the global ordering of the crystalline or polycrystalline structure on the substrate surface. The last step of the Cascade Crystallization process is drying/crystallization, which converts the lyotropic liquid crystal into a solid crystal dielectric layer. The term Cascade Crystallization process is used to refer to the chemical modification and four ordering steps as a combination process.

The Cascade Crystallization process is used for production of thin crystalline dielectric layers. The dielectric layer produced by the Cascade Crystallization process has a global order which means that a direction of the crystallographic axis of the layer over the entire substrate surface is controlled by the deposition process. Molecules of the deposited material are packed into supramolecules with a limited freedom of diffusion or motion. The thin crystalline dielectric layer is characterized by an interplanar spacing of 3.4±0.3 Å in the direction of one of the optical axes.

In another aspect, the present disclosure provides a capacitor, an example of which is shown in FIG. 1. The capacitor generally includes a first electrode (1), a second electrode (2), and a crystal dielectric layer (3) disposed between said first and second electrodes and wherein said crystal dielectric layer comprises sublayers (4) which are characterized by electronic polarizability and have supramolecules formed with the aromatic polycyclic conjugated Cores, of any of the types described herein, and isotropic insulating sublayers (5) formed with the A-groups which serve as the isolating groups described above. These insulating sublayers prevent occurrence of percolation with formation of continuous electrically conductive channels under action of electric field.

The electrodes 1, 2 may be flat and planar and positioned parallel to each other. Alternatively, the electrodes may be planar and parallel, but not necessarily flat, e.g., they may be coiled, rolled, bent, folded, or otherwise shaped to reduce the overall form factor of the capacitor. It is also possible for the electrodes to be non-flat, non-planar, or non-parallel or some combination of two or more of these. By way of example and not by way of limitation, a spacing d between the electrodes 1, 2 which may correspond to the thickness of the crystal dielectric layer 106 may range from about 1 µm to about 10 000 µm. As noted in Equation (2) above, the maximum voltage $V_{bd}$ between the electrodes 102, 103 is approximately the product of the breakdown field and the electrode spacing d. For example, if, $E_{bd}$=0.1 V/nm and the spacing d between the electrodes 1, 2 is 10,000 microns (100,000 nm), the maximum voltage $V_{bd}$ would be 100,000 volts.

The electrodes 1, 2 may have the same shape as each other, the same dimensions, and the same area A. By way of example, and not by way of limitation, the area A of each electrode 102,104 may range from about 0.01 m² to about 1000 m². By way of example and not by way of limitation, for rolled capacitors, electrodes up to, e.g., 1000 m long and 1 m wide are manufacturable with roll-to-roll processes similar to those used to manufacture magnetic tape or photographic film.

These ranges are non-limiting. Other ranges of the electrode spacing d and area A are within the scope of the aspects of the present disclosure.

If the spacing d is small compared to the characteristic linear dimensions of electrodes (e.g., length and/or width), the capacitance C of the capacitor may be approximated by the formula:

$$C = \kappa \in_o A/d, \quad (3)$$

where $\in_o$ is the permittivity of free space (8.85×10⁻¹² Coulombs²/(Newton·meter²)) and κ is the dielectric constant of the dielectric layer. The energy storage capacity U of the capacitor may be approximated as:

$$U = \tfrac{1}{2} CV_{bd}^2 \quad (4)$$

which may be rewritten using equations (2) and (3) as:

$$U = \tfrac{1}{2} \kappa \in_o A E_{bd}^2 d \quad (5)$$

The energy storage capacity U is determined by the dielectric constant κ, the area A, and the breakdown field $E_{bd}$. By appropriate engineering, a capacitor or capacitor bank may be designed to have any desired energy storage capacity U. By way of example, and not by way of limitation, given the above ranges for the dielectric constant κ, electrode area A, and breakdown field $E_{bd}$ a capacitor in accordance with aspects of the present disclosure may have an energy storage capacity U ranging from about 500 Joules to about 2×10¹⁶ Joules.

For a dielectric constant κ ranging, e.g., from about 100 to about 1,000,000 and constant breakdown field $E_{bd}$ between, e.g., about 0.1 and 0.5 V/nm, a capacitor of the type described herein may have a specific energy capacity per unit mass ranging from about 10 W·h/kg up to about 100,000 W·h/kg, though implementations are not so limited.

In order that aspects of the present disclosure may be more readily understood, reference is made to the following examples, which are intended to be illustrative of the invention, but are not intended to be limiting the scope.

EXAMPLE 1

This Example describes synthesis of the disclosed organic compound (see, general structural formula 40 in Table 5) according following structural scheme:

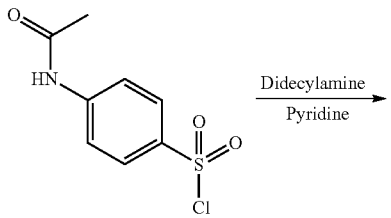

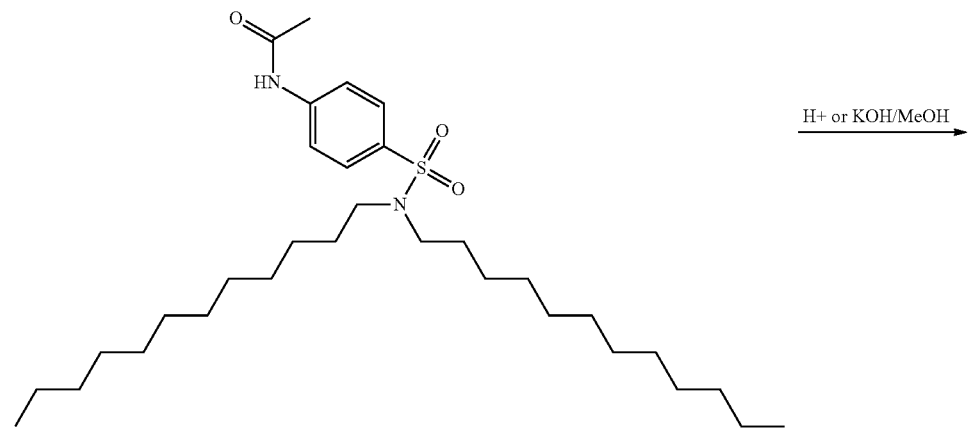

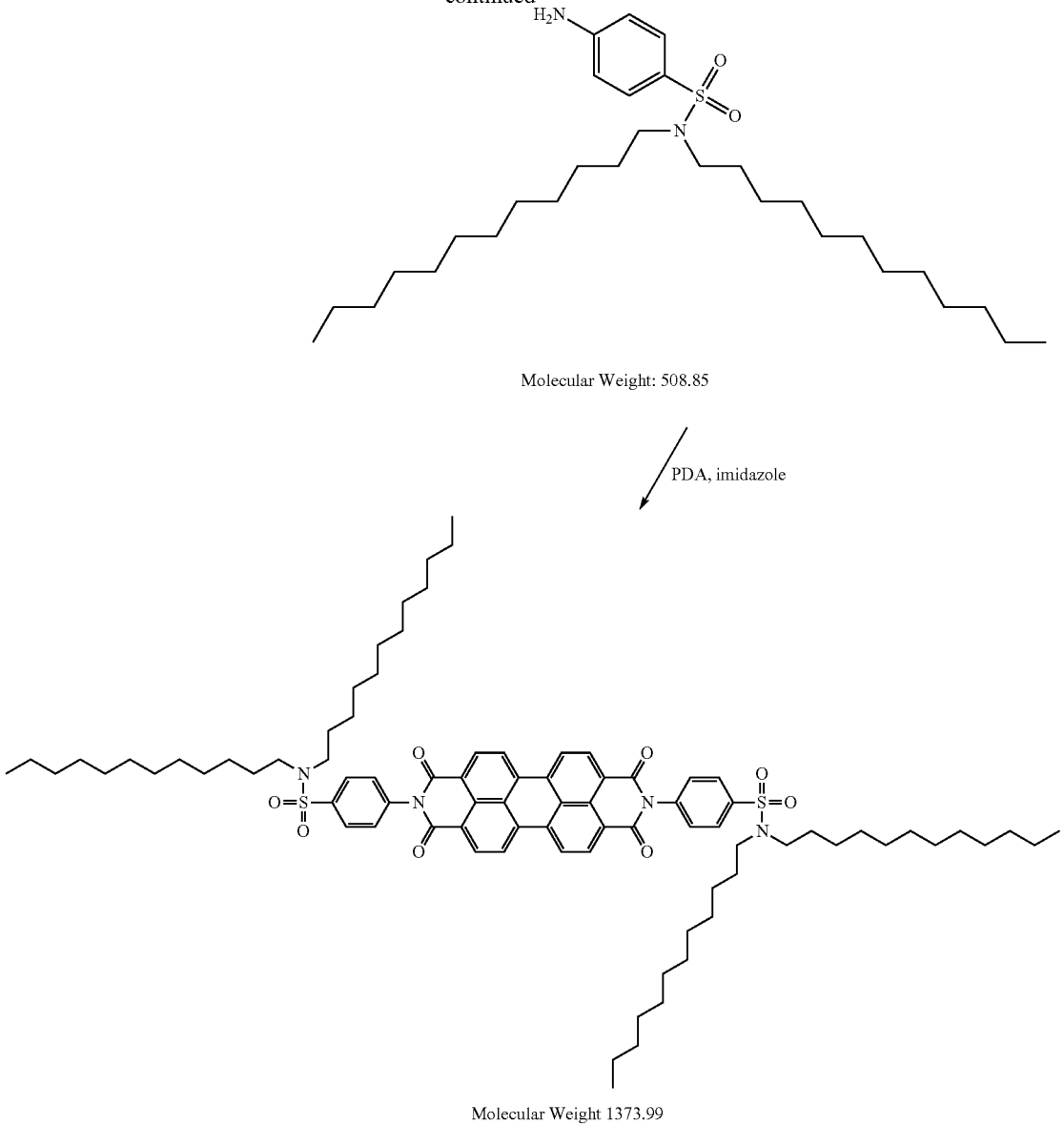

Molecular Weight: 508.85

PDA, imidazole

Molecular Weight 1373.99

N,N-Didodecyl-4-Acetamidobenzenesulfonamine: N-acetylsulfanilyl chloride (3.3 g, 14.12 mmol) and didodecylamine (4.77 g, 13.48 mmol) were added to a 100 mL flask sealed with a rubber septa under nitrogen. The flask was cooled on an ice bath, and pyridine (18 mL) cooled on an ice bath was added to the chloride amine flask via syringe. The flask was placed in the refrigerator overnight.

The mixture was diluted with ethyl acetate (150 mL) and filtered into a separatory funnel (note, starting didodecylamine is poorly soluble so most unreacted amine is removed at this step). The organic layer was washed 3× with water, 3× dilute HCl, 1× sat. NaHCO₃, 1× brine, dried over MgSO₄, and then filtered through a ½" silica gel pad, rinsing with 50 mL ethyl acetate. The solvent was removed under reduced pressure, and recrystallized in hexane (by storing in a refrigerator for several hours). The solid was filtered, rinsed with cold hexanes, and allowed to dry with hood airflow. 2.95 g of off white crystals recovered, 40% yield.

4-Amino N,N-didodecylbenzenesulfonamine: A 100 mL flask was charged with N,N-Didodecyl-4-Acetamidobenzenesulfonamine (2.0 g, 3.63 mmol), to which was added a solution of KOH (2.037 g, 36.3 mmol) dissolved in water (2 ml), methanol (10 mL) and THF (10 mL). The solution was heated to reflux for 4 hours. Reaction was complete by tlc (100% EtAc). Cooled to RT, extracted 3×50 mL hexanes, 1×25 mL EtAc, washed the combined organic layers with water, and then brine, dried over MgSO₄, and filtered through ¼" silica gel pad, rising with EtAc (50 mL). Dried over reduced pressure and recovered 1.82 g of beige solid (99% yield).

General Structural Formula 40 in Table 5: (Re: Robb and Hawker, J. Org. Chem. 2014, 79, 6360-6365, which is incorporated herein by reference) A 2 necked 50 mL flask was charged with 4-Amino N,N-didodecylbenzenesulfonamine (1.7 g, 3.35 mmol), and powdered mixture of perylene-3,4,9,10-tetracarboxylic dianhydride (0.657 g, 1.675 mmol) and imidazole (7 g). The flask was purged with $N_2$ for 10 minutes, and then placed in an oil bath (130 C) with stirring for 20 hrs (tlc shows absence of starting amine).

The cooled mixture was dissolved in methylene chloride, washed with 1M HCl, the aqueous layer being further washed 3× methylene chloride, adding a minimum amount of IPA to reduce the emulsion. The following procedures are in summary carried out: drying of the organic layer over MgSO$_4$, filtering of through a 1" silica gel pad, rinsing with of 10% of methanol/CH$_2$C$_{12}$, and removing the solvent under reduced pressure. Recovered weight (mass) was equal to 2 g (85%).

EXAMPLE 2

This Example describes synthesis of the disclosed organic compound (see, general structural formula 41 in Table 5) according following structural scheme:

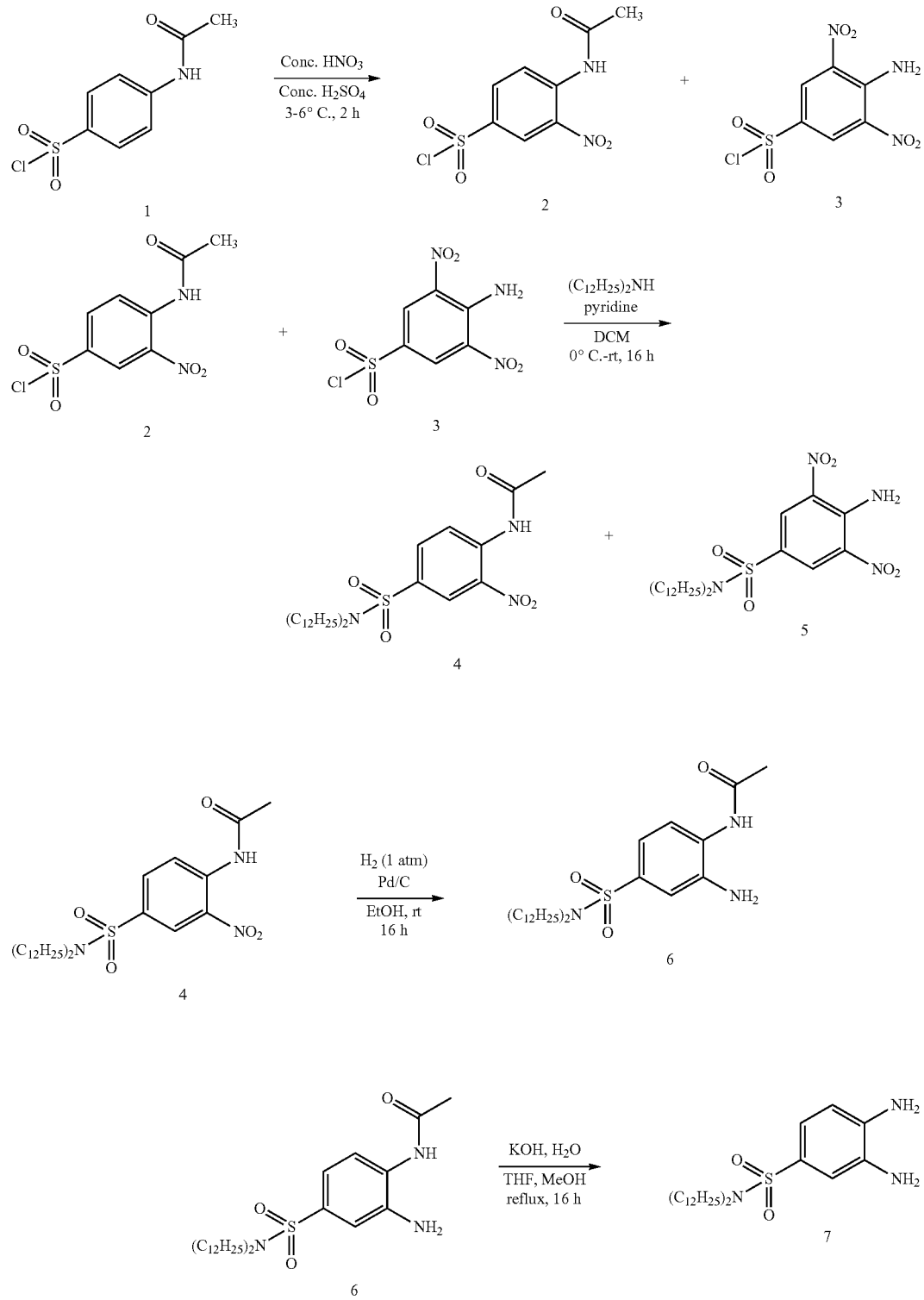

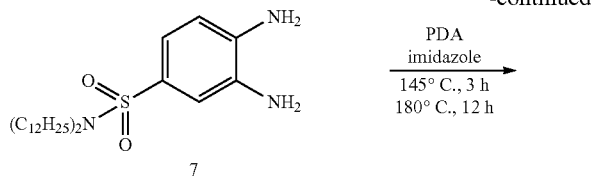

-continued

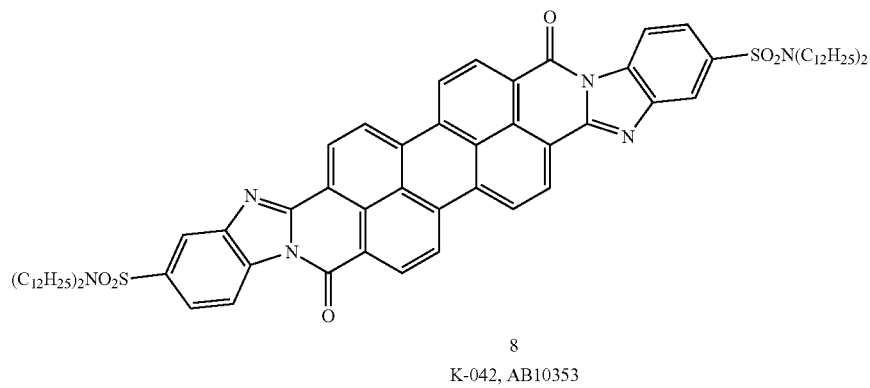

K-042, AB10353

To a cooled (ice-water) concentrated H₂SO₄ (240.0 mL) was added sulfonyl chloride 1 (50.0 g, 0.21 mol, 1.0 ea) in portions. The mixture was stirred at 0° C. until a clear solution. A pre-mixed mixture of concentrated H₂SO₄ (98%, 30.0 mL) and concentrated HNO₃ (70%, 30.0 mL) was added slowly to maintain reaction temperature below 10° C. After addition, the reaction mixture was stirred at 10° C. for 4.0 hrs, poured into ice-water (2000 mL). The precipitate was brought into hot benzene (60° C., 1000 mL), separated organic layer from water, dried over Na₂SO₄, filtered and concentrated to give 47.0 g (77%) of a mixture mono-nitro compound 2 and bis-nitro 3 (2:3=3:2 by NMR). ¹H NMR (300 MHz, CDCl₃) δ 10.67 (bs, 1H), 9.19-9.16 (d, J=9.0 Hz, 1H), 9.12 (s, 1H), 9.04 (bs, 2H), 8.91-8.90•(d, J=3.0 Hz, 1H), 8.26-8.22 (dd, J=9.0 Hz, J=3.0 Hz, 1H), 2.38 (s, 3H).

To a solution of didodecylamine (25.0 g, 70.7 mmol, eq) in dichloromethane (400 mL), was added pyridine (35.1 g, 440.0 mmol, 5.0 eq) and a mixture of mono-nitro 2 and bis-nitro 3 (20.0 g, 68.9 mmol, 1.0 eq) at 0° C. The resulting mixture was stirred at room temperature for 16 hrs, diluted with dichloromethane (400 mL), washed with water (2×200 mL), brine (200 mL), dried over dried over Na₂SO₄, filtered and concentrated to give a residue. The crude product was purified by flash chromatography column (EtOAc/Hexane=3/10 to 1/2) to give 6.3 g (15.4%) of mono-nitro compound 4 as a yellow solid and 11.0 g (26.7%) of bis-nitro 5 as a red-yellow solid. Compound 4: ¹H NMR (300 MHz, CDCl₃) δ 10.50 (bs, 1H), 8.99-8.96 (d, J=9.0 Hz, 1H), 8.64 (s, 1H), 8.02-8.98 (d, J=10.8 Hz, 1H), 3.16-3.11 (t, J=7.8 Hz, 4H), 2.34 (s, 3H), 1.61-1.44 (m. 4H), 1.40-1.15 (m, 36H), 1.00-0.80 (t, J=6.0 Hz, 6H).

To a suspension of the mono-nitro compound 4 (6.3 g, 10.6 mmol, 1.0 eq) in ethanol (700 mL) was added Pd/C (10% on carbon, 50% wet, 1.3 g, 10 w %). The mixture was degassed (vacuum and fill with H₂) three times, and stirred at room temperature under 1 atm H₂ for 16 hrs, filtered through a pad of Celite. The filtrate was concentrated to give 6.0 g (100%) of the amine 6 as a yellow solid. ¹H·NMR· (300·MHz, CDCl₃) δ 7.41-7.38 (d, J=8.1 Hz, 1H), 7.32 (bs, 1H), 7.20 (s, 1H), 7.18-7.15 (dd, J=8.4 Hz, J=1.8 Hz, 1H), 3.95 (bs, 2H), 3.08-3.03 (t, J=7.5 Hz, 4H), 1.45-1.40 (m, 4H), 1.35-1.15 (m, 36H), 0.92-0.80 (t, J=6.3 Hz, 6H).

To a solution of the amine 6 (6.0 g, 10.6 mmol, 1.0 eq) in THF (30 mL) and MeOH (30 mL) was added a solution of KOH (6.0 g, 110.0 mmol, 10.0 eq) in water (5.0 mL). The mixture was stirred at reflux for 6 hrs and concentrated. The residue was partitioned between EtOAc (100 mL) and water (100 mL). Organic layer was separated, dried over Na₂SO₄, filtered and concentrated to give a residue. The crude product was purified by flash chromatography column (EtOAc/Hexane=1/1) to give 3.5 g (63.1%) of diamine 7 as a light yellow solid. ¹H NMR (300 MHz, CDCl₃) δ 7.18-7.14 (dd, J=7.8 Hz, J=1.8 Hz, 1H), 7.12 (s, 1H), 6.72-6.69 (d, J=8.1 Hz, 1H), 3.07-3.02 (t, J=7.2 Hz, 4H), 1.45-1.40 (m, 4H), 1.35-1.15 (m, 36H), 1.00-0.80 (t, J=6.0 Hz, 6H).

The diamine 7 (3.4 g, 6.5 mmol, 2.2 equ), 3,4,9,10-perylenetetracarboxylic dianhydride (1.2 g, 2.9 mmol, 1.0 eq) and imidazole (31.0 g, 455.0 mmol, 70 eq to diamine) were mixed well in a 200 mL round-bottom flask equipped with a rotavap bump guard. The mixture was degased (vacuum and fill with N₂) three times and stirred at 145° C. for 3 hrs, 180° C. for 12 hrs. After cooling to rt, the reaction mixture was crushed into water (500 mL), stirred for 1 hour, and filtered through a filter paper to collected precipitate which was washed with water (4×50 mL) and ethanol (4×50 mL), dried on a high vacuum to give 3.7 g (91.5%) of the diamidine 8 as a dark purple solid. ¹H NMR (300 MHz, CDCl₃) δ 8.80-8.40 (m, 8H), 8.22-8.06 (m, 2H), 7.70-7.60 (m, 4H), 3.20-3.00 (m, 8H), 1.60-1.40 (m, 8H), 1.40-1.10 (m, 72H), 0.96-0.80 (m, 12H).

EXAMPLE 3

This example describes synthesis of the disclosed organic compound (see, general structural formula 42 in Table 5) according following structural scheme:

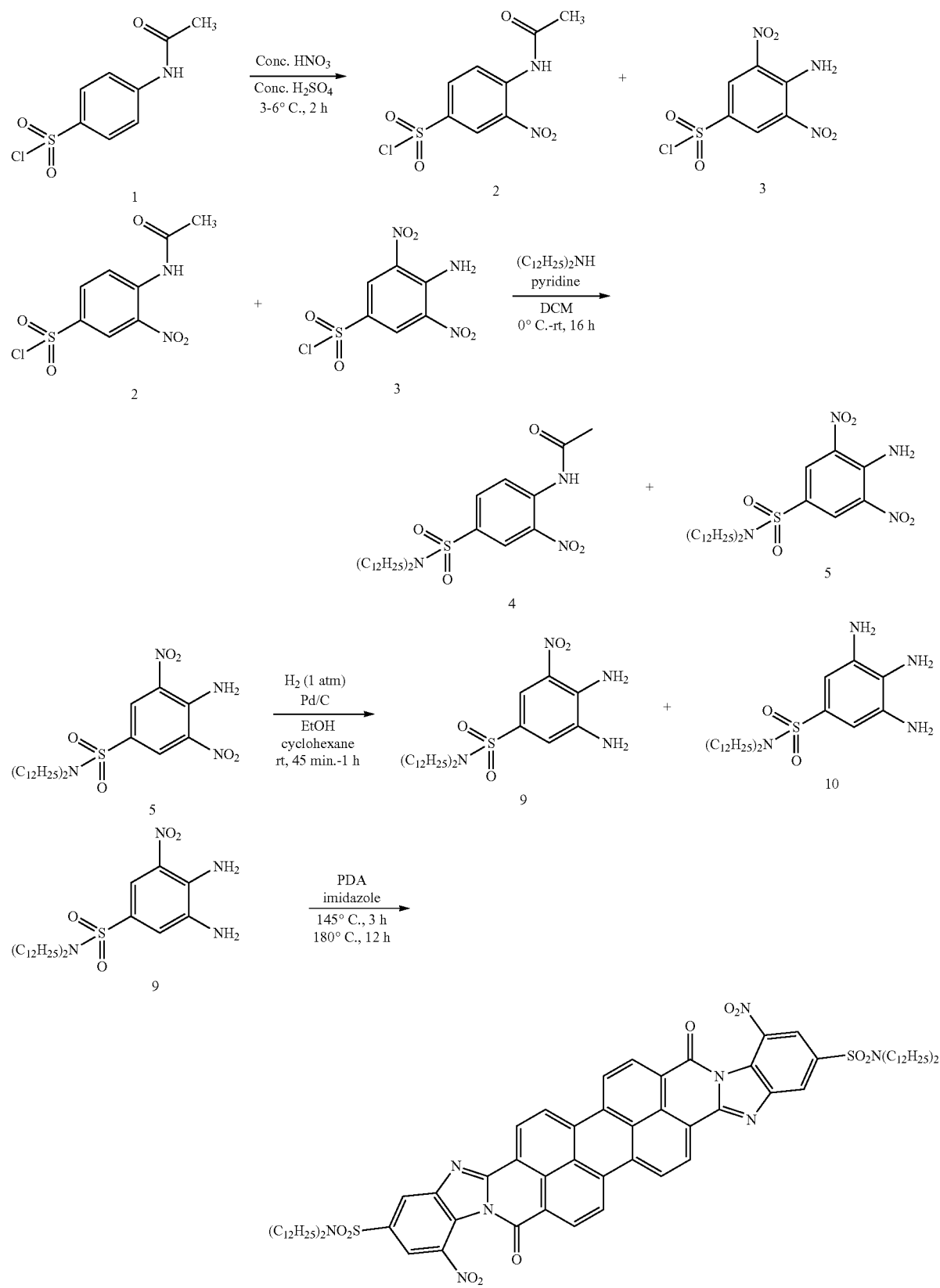

Sulfonyl chloride 1 (50.0 g, 0.21 mol, 1.0 ea) was added in portions to cooled (ice-water) concentrated $H_2SO_4$ (240.0 mL). The mixture was stirred at 0° C. until a clear solution. A pre-mixed mixture of concentrated $H_2SO_4$ (98%, 30.0 mL) and concentrated $HNO_3$ (70%, 30.0 mL) was added slowly to maintain reaction temperature below 10° C. After addition, the reaction mixture was stirred at 10° C. for 4.0 hrs, poured into ice-water (2000 mL). The precipitate was brought into hot benzene (60° C., 1000 mL), separated organic layer from water, dried over $Na_2SO_4$, filtered and concentrated to give 47.0 g (77%) of a mixture mono-nitro compound 2 and bis-nitro compound 3 (2:3=3:2 by NMR). $^1$H NMR (300 MHz, $CDCl_3$) δ 10.67 (bs, 1H), 9.19–9.16 (d, J=9.0 Hz, 1H), 9.12 (s, 1H), 9.04 (bs, 2H), 8.91–8.90 (d, J=3.0 Hz, 1H), 8.26–8.22 (dd, J=9.0 Hz, J=3.0 Hz, 1H), 2.38 (s, 3H).

To a solution of didodecylamine (25.0 g, 70.7 mmol, eq) in dichloromethane (400 mL), was added pyridine (35.1 g, 440.0 mmol, 5.0 eq) and a mixture of mono-nitro 2 and bis-nitro 3 (20.0 g, 68.9 mmol, 1.0 eq) at 0° C. The resulting mixture was stirred at room temperature for 16 hrs, diluted with dichloromethane (400 mL), washed with water (2×200 mL), brine (200 mL), dried over dried over $Na_2SO_4$, filtered and concentrated to give a residue. The crude product was purified by flash chromatography column (EtOAc/Hexane=3/10 to 1/2) to give 6.3 g (15.4%) of mono-nitro compound 4 as a yellow solid and 11.0 g (26.7%) of bis-nitro 5 as a red-yellow solid. 5: $^1$H NMR (300 MHz, $CDCl_3$) δ 8.89 (s, 2H), 8.76 (bs, 2H), 3.18–3.13 (t, J=7.5 Hz, 4H), 2.34 (s, 3H), 1.61–1.44 (m, 4H), 1.40–1.15 (m, 36H), 0.90–0.80 (t, J=6.3 Hz, 6H).

To a solution of the bis-nitro compound 5 (8.6 g, 14.4 mmol, 1.0 eq) in ethanol (800 mL) and cyclohexane (800 mL) was added Pd/C (10% on carbon, 50% wet, 0.9 g, 5 w %). The mixture was degassed (vacuum and fill with $H_2$) three times, and stirred at room temperature under 1 atm $H_2$ for 1 hour, filtered through a Celite. The filtrate was concentrated to give 4.5 g (55.0%) of the diamine 9 as a yellow-red solid, and 2.3 g of a intermediate as a yellow solid which was hydrogenated again following the above procedure to give 1.3 g (16.8%) of the triamine 10 as a dark-brown solid. Compound 9: $^1$H NMR (300 MHz, $CDCl_3$) δ 8.18 (s, 1H), 7.28 (s, 1H), 6.38 (s, 2H), 3.62 (s, 2H), 3.12–3.06 (t, J=8.6 Hz, 4H), 1.60–1.45 (m, 4H), 1.38–1.15 (m, 36H), 0.92–0.82 (t, J=6.3 Hz, 6H).

Mixed well the diamine 9 (4.5 g, 7.9 mmol, 2.2 equ), 3,4,9,10-perylenetetracarboxylic dianhydride (1.4 g, 3.6 mmol, 1.0 eq) and imidazole (38.0 g, 550.0 mmol, 70 eq to diamine) into a 200 mL round-bottom flask equipped with a rotavap bump guard. The mixture was degased (vacuum and fill with $N_2$) three times and stirred at 145° C. for 3 hrs, 180° C. for 12 hrs. After cooling to rt, the reaction mixture was crushed into water (600 mL), stirred for 1 hour, and filtered through a filter paper to collected precipitate which was washed with water (4×50 mL) and ethanol (4×50 mL), dried on a high vacuum to give 5.2 g (99.0%) of the diamidine 11 as a dark purple solid.

EXAMPLE 4

This example describes synthesis of the disclosed organic compound (see, general structural formula 43 in Table 5) according following structural scheme:

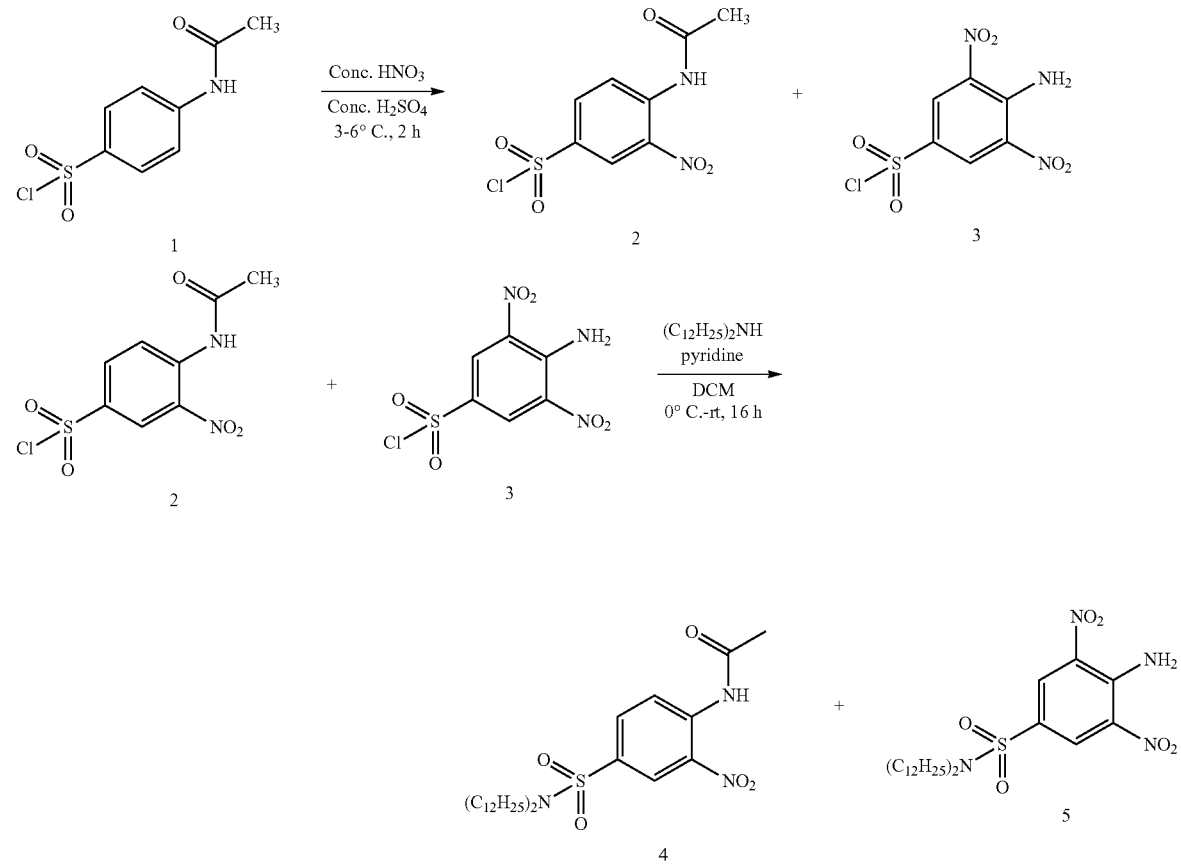

-continued

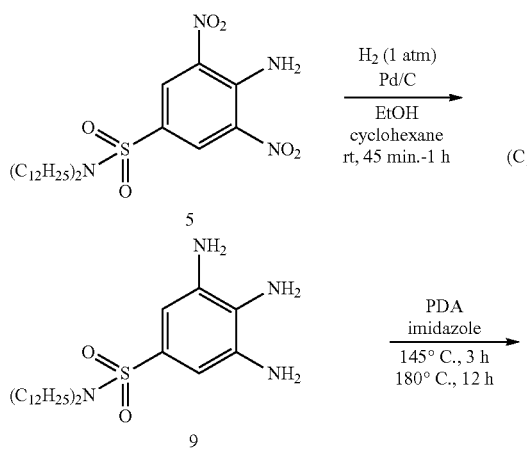

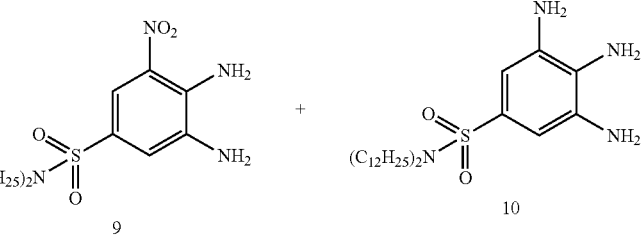

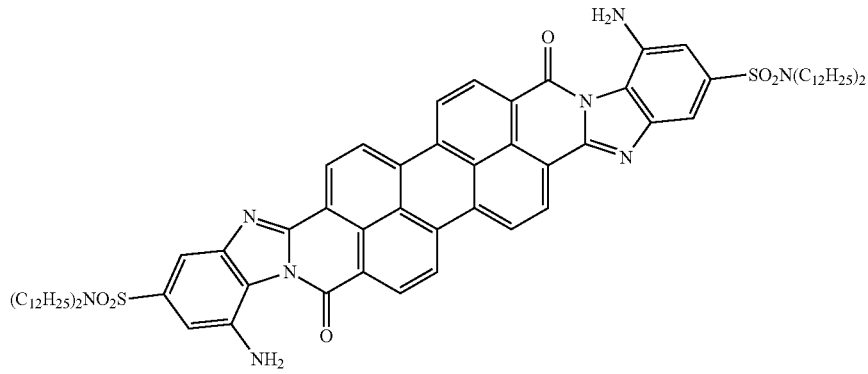

12
K-074, AB10392

To a cold (ice-water) con. H₂SO₄ (240.0 mL) was added sulfonyl chloride 1 (50.0 g, 0.21 mol, 1.0 ea) in portions. The mixture was stirred at 0° C. until a clear solution. A pre-mixed mixture of concentrated H₂SO₄ (98%, 30.0 mL) and concentrated HNO₃ (70%, 30.0 mL) was added slowly to maintain reaction temperature below 10° C. After addition, the reaction mixture was stirred at 10° C. for 4.0 hrs, poured into ice-water (2000 mL). The precipitate was brought into hot benzene (60° C., 1000 mL), separated organic layer from water, dried over Na₂SO₄, filtered and concentrated to give 47.0 g (77%) of a mixture mono-nitro compound 2 and bis-nitro compound 3 (2:3=3:2 by NMR). $^1$H NMR (300 MHz, CDCl₃) δ 10.67 (bs, 1H), 9.19–9.16 (d, J=9.0 Hz, 1H), 9.12 (s, 1H), 9.04 (bs, 2H), 8.91–8.90 (d,☐J=3.0 Hz, 1H), 8.26–8.22 (dd, J☐=9.0 Hz,☐J=3.0 Hz, 1H), 2.38 (s, 3H).

To a solution of didodecylamine (25.0 g, 70.7 mmol, eq) in dichloromethane (400 mL), was added pyridine (35.1 g, 440.0 mmol, 5.0 eq) and a mixture of mono-nitro 2 and bis-nitro 3 (20.0 g, 68.9 mmol, 1.0 eq) at 0° C. The resulting mixture was stirred at room temperature for 16 hrs, diluted with dichloromethane (400 mL), washed with water (2×200 mL), brine (200 mL), dried over dried over Na₂SO₄, filtered and concentrated to give a residue. The crude product was purified by flash chromatography column (EtOAc/Hexane=3/10 to 1/2) to give 6.3 g (15.4%) of mono-nitro compound 4 as a yellow solid and 11.0 g (26.7%) of bis-nitro 5 as a red-yellow solid. 5: $^1$H NMR (300 MHz, CDCl₃) δ 8.89 (s, 2H), 8.76 (bs, 2H), 3.18–3.13 (t, J=7.5 Hz, 4H), 2.34 (s, 3H), 1.61–1.44 (m, 4H), 1.40–1.15 (m, 36H), 0.90–0.80 (t, J=6.3 Hz, 6H).

To a solution of the bis-nitro compound 5 (8.6 g, 14.4 mmol, 1.0 eq) in ethanol (800 mL) and cyclohexane (800 mL) was added Pd/C (10% on carbon, 50% wet, 0.9 g, 5 w %). The mixture was degassed (vacuum and fill with H₂) three times, and stirred at room temperature under 1 atm H₂ for 1 hour, filtered through a Celite. The filtrate was concentrated to give 4.5 g (55.0%) of the diamine 9 as a yellow-red solid, and 2.3 g of a intermediate as a yellow solid which was hydrogenated again following the above procedure to give 1.3 g (16.8%) of the triamine 10 as a dark-brown solid. Compound 10: $^1$H NMR (300 MHz, CDCl₃) δ 6.77 (s, 2H), 3.55–3.35 (m, 6H), 3.06–3.00 (t, J=7.5 Hz, 4H), 1.55–1.42 (m, 4H), 1.38–1.18 (m, 36H), 0.90–0.86 (t, J=6.3 Hz, 6H), 2.98–2.94 (m, 2H), 2.68–2.64 (m, 2H), 2.60 (s, 3H), 2.30 (s, 3H).

Mixed well the diamine 10 (0.5 g, 0.88 mmol, 2.2 equ), 3,4,9,10-perylenetetracarboxylic dianhydride (0.16 g, 0.40 mmol, 1.0 eq) and imidazole (4.2 g, 61.6 mmol, 70 eq to diamine) into a 100 mL round-bottom flask equipped with a rotavap bump guard. The mixture was degased (vacuum and fill with N₂) three times and stirred at 145° C. for 3 hrs, 180° C. for 12 hrs. After cooling to rt, the reaction mixture was crushed into water (200 mL), stirred for 1 hour, and filtered through a filter paper to collected precipitate which was washed with water (4×30 mL) and ethanol (4×30 mL), dried on a high vacuum to give 0.5 g (89.5%) of the diamidine 12 as a dark solid.

EXAMPLE 5

This example describes synthesis of the disclosed organic compound (see, general structural formula 44 in Table 5) according following structural schemes:

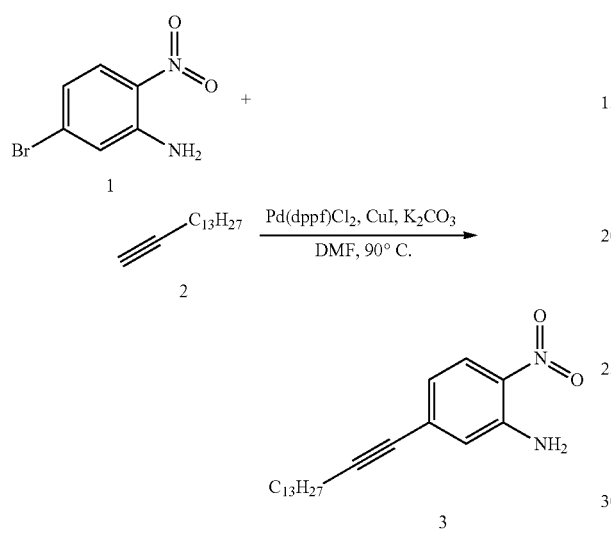

To anhydrous DMF (15.0 mL) was added compound 1 (3.3 g, 15 mmol, 1.0 eq), compound 2 (4.8 mL, 18 mmol, 1.2 eq), Pd(dppf)Cl$_2$ (0.24 g, 0.3 mmol, 0.02 eq), CuI (0.12 g, 0.6 mmol, 0.04 eq) and K$_2$CO$_3$ (4.2 g, 30 mmol, 2.0 eq). The mixture was degassed under vacuum and purged with N$_2$ three times. The reaction was stirred at 90° C. for 8.0 hrs. The mixture was cooled down and EA (15 mL) was added to dilute. Filtered off the solid and poured the filtrate into water, extracted with EA (3×10 mL). Washed organic phase with water (10 mL) and brine (10 mL), dried over MgSO$_4$, filtered and concentrated. The residue was treated with a sil-gel column to give 2.1 g (40%) of product 3 as a dark yellow solid. $^1$H NMR (300 MHz, CDCl$_3$) δ 8.17 (s, 1H), 7.34 (d, 1H), 6.70 (d, 1H), 6.19 (s, 2H), 2.36 (t, 2H), 1.26-1.56 (m, 22H), 0.87 (t, 3H).

To EA (2.0 mL) was added compound 3 (500.0 mg, 1.44 mmol, 1.0 eq) and Pd/C (50.0 mg, 0.1 eq). The mixture was stirred at room temperature under H$_2$-balloon for 20 min. Filtered off solid, concentrated to give compound 4 346 mg (80%) as light yellow solid. $^1$H NMR (300 MHz, CDCl$_3$) δ 6.61 (d, 1H), 6.50 (d, 1H), 6.54 (s, 1H), 7.86 (t, 2H), 1.25 (m, 22H), 0.88 (t, 3H).

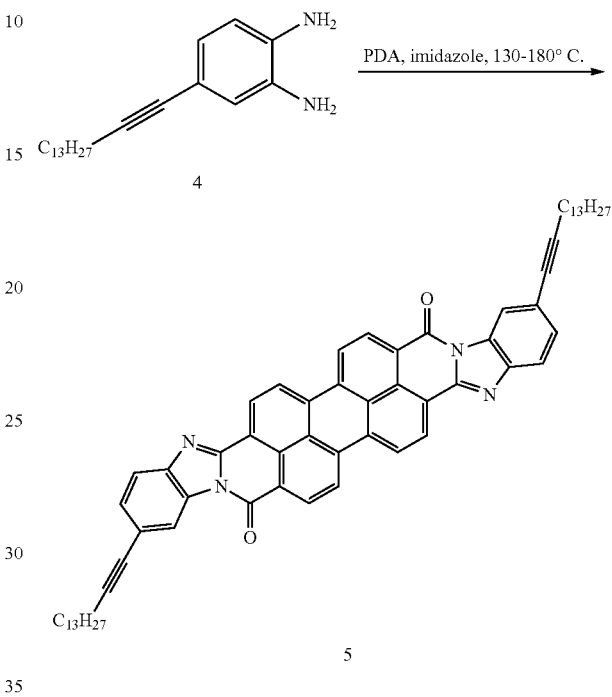

To a 25 mL flask was added compound 4 (758 mg, 2.4 mmol, 2.2 eq), PDA (429 mg, 1.1 mmol, 1 eq) and imidazole (5.2 g, 77 mmol, 70 eq). The mixture was degassed under vacuum and purged with N$_2$ three times. The reaction was stirred at 130° C. for 3 hrs and 180° C. for 12 more hrs. The dark purple mixture was cooled down. The solid was washed with water (3×2 mL) and EtOH (3×2 mL), vacuum dried to give product 5 912 mg (40%) as a dark purple solid. $^1$H NMR (300 MHz, CDCl$_3$) not available.

Example 6

This example describes synthesis of the disclosed organic compound (see, general structural formula 46 in Table 5) according following structural schemes:

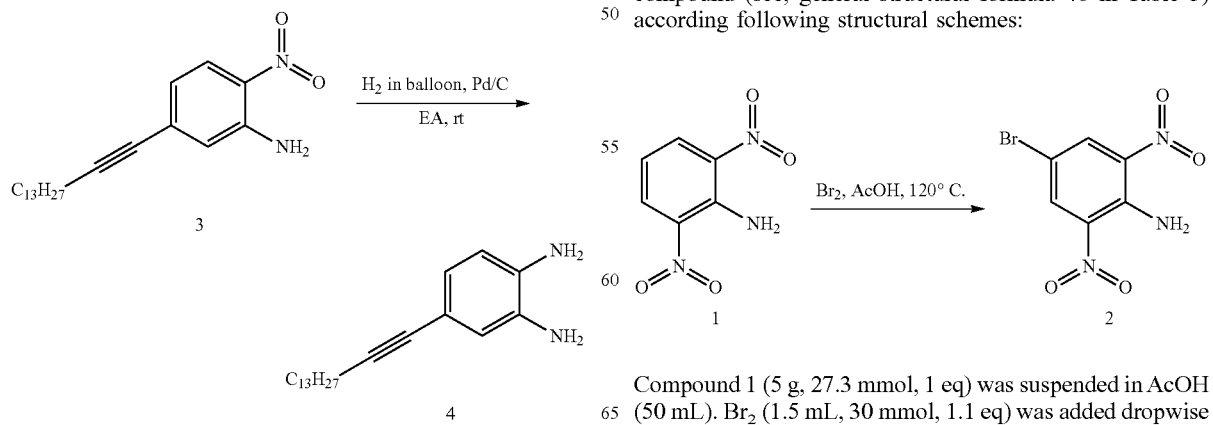

Compound 1 (5 g, 27.3 mmol, 1 eq) was suspended in AcOH (50 mL). Br$_2$ (1.5 mL, 30 mmol, 1.1 eq) was added dropwise at rt. After addition, the temperature was increased to 120° C. and kept stirring at this temperature for 2 hrs. The mixture was poured into ice water. The precipitate was filtered, washed with water and dried under vacuum to give product 2 6.8 g (95%) as a yellow solid. $^1$H NMR (300 MHz, CDCl$_3$) not available.

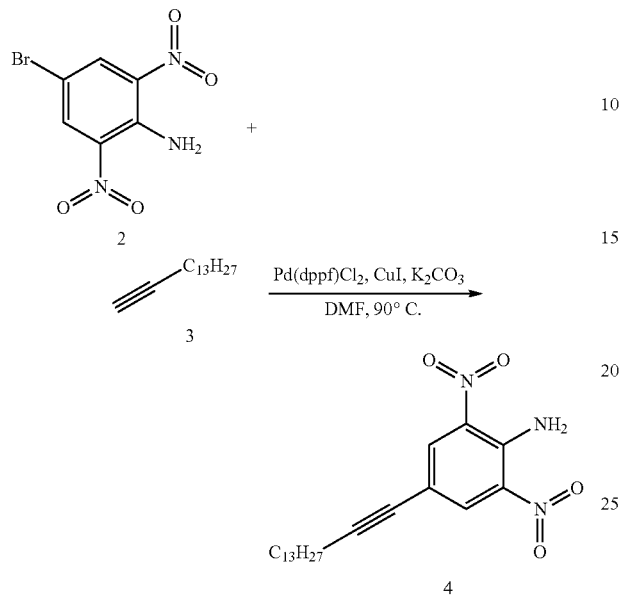

To anhydrous DMF (10.0 mL) was added compound 2 (2.0 g, 7.6 mmol, 1.0 eq), compound 3 (2.4 mL, 9.1 mmol, 1.2 eq), Pd(dppf)Cl$_2$ (0.13 g, 0.15 mmol, 0.02 eq), CuI (0.06 g, 0.3 mmol, 0.04 eq) and K$_2$CO$_3$ (2.1 g, 15 mmol, 2.0 eq). The mixture was degassed under vacuum and purged with N$_2$ three times. The reaction was stirred at 90° C. for 8.0 hrs. The mixture was cooled down and EA (10 mL) was added to dilute. Filtered off the solid and poured the filtrate into water, extracted with EA (3×5 mL). Washed organic phase with water (5 mL) and brine (5 mL), dried over MgSO$_4$, filtered and concentrated. The residue was treated with a sil-gel column to give 520 mg (17%) of product 4 as a dark yellow solid. $^1$H NMR (300 MHz, CDCl$_3$) δ 8.53 (s, 2H), 2.37 (t, 2H), 1.26-1.55 (m, 22H), 0.87 (t, 3H).

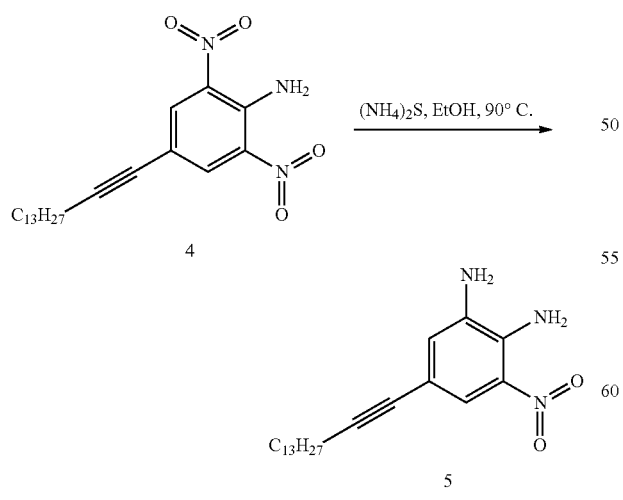

To EtOH (1.0 mL) was added compound 4 (60 mg, 0.15 mmol, 1.0 ea) and ammonium sulfide (104 mg 20% water solution, 0.3 mmol, 2.0 eq). The mixture was stirred at 80° C. for 1 hr. Refilled 2.0 eq ammonium sulfide. The received mixture again was stirred at 80° C. for 1 hr. The mixture was concentrated, diluted with EA, washed with water and brine. Organic phase was collected, concentrated and separated through a column to give product 5 21.8 mg (40%) as a dark red solid. $^1$H NMR (300 MHz, CDCl$_3$) δ 7.81 (s, 1H), 6.94 (s, 1H), 6.03 (s, 2H), 3.26 (s, 2H), 2.36 (t, 2H), 1.26-1.53 (m, 22H), 0.87 (t, 3H).

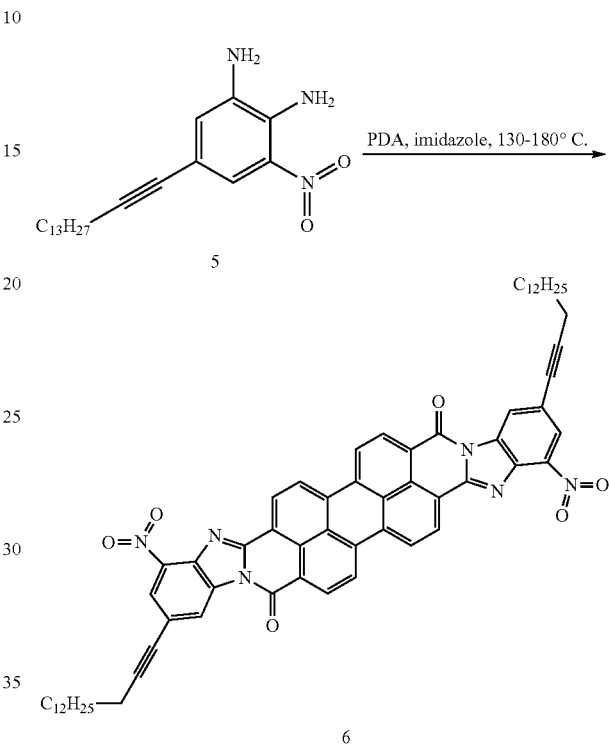

To a 5 mL vial was added compound 5 (21.8 mg, 0.06 mmol, 2.2 eq), PDA (10.8 mg, 0.028 mmol, 1 eq) and imidazole (131 g, 1.93 mmol, 70 eq). The mixture was degassed under vacuum and purged with N$_2$ three times. The reaction was stirred at 130° C. for 3 hrs and 180° C. for 12 more hrs. The dark purple mixture was cooled down. The solid was washed with water (3×0.5 mL) and EtOH (3×0.5 mL), vacuum dried to give product 6 27 mg (45%) as a dark purple solid. $^1$H NMR (300 MHz, CDCl$_3$) not available.

EXAMPLE 6

This example describes synthesis of the disclosed organic compound (see, general structural formula 46 in Table 5) according following structural schemes:

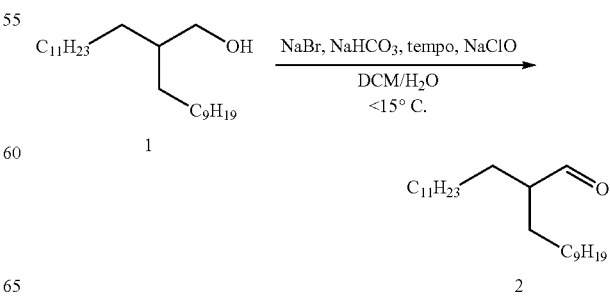

To H₂O (10.0 mL) was added NaHCO₃ (1.7 g, 20.2 mmol, 30 g/mol eq) and NaBr (280.0 mg, 2.7 mmol, 5 g/mol eq). The mixture was stirred to form a clear solution. Compound 1 (20 g, 56.4 mmol, 1 eq) in DCM (70 mL) and tempo (340.0 mg, 0.6 g/mol) were added to the clear solution. The two-phase mixture was cooled down to 10° C. The NaClO solution (70.5 mL, 0.8 N, 1 eq) was added dropwise with vigorously stirring. After addition, removed ice bath and kept stirring at room temperature for 30 min. Collected DCM phase, extracted with DCM (25 mL×2), combined organic phase, washed with water and brine, dried over MgSO₄ and concentrated to give compound 2 18 g (90%) as a colorless oil. ¹H NMR (300 MHz, CDCl₃) not available.

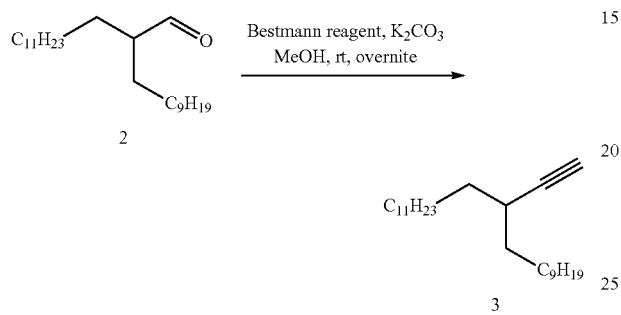

To MeOH (60.0 mL) was added freshly made compound 2 (18 g, 51.1 mmol, 2.0 eq), bestmann reagent (5.0 g, 25.6 mmol, 1.0 eq) and K₂CO₃ (7.1 g, 51.1 mmol, 2.0 eq). The mixture was stirred at room temperature for 24 hrs. EA (30.0 mL) was added to dilute the mixture. Mixture was filtered to separate solid sediment (precipitate). Washed with EA. The filtrate was concentrated. The residue was separated through a column to afford compound 3 7.4 g (82%) as white solid. ¹H NMR (300 MHz, CDCl₃) δ 2.15 (m, 1H), 2.03 (s, 1H), 1.26-1.41 (m, 40H), 0.87 (t, 6H).

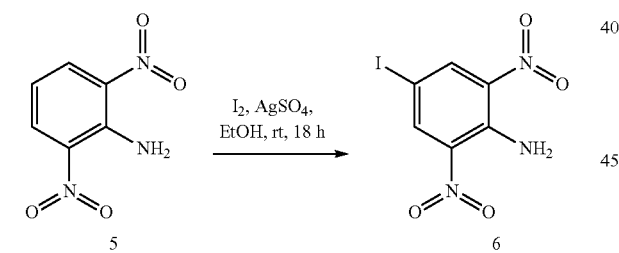

To EtOH (40.0 mL) was added compound 5 (4.2 g, 23.0 mmol, 1.0 eq), AgSO₄ (10.0 g, 32.1 mmol, 1.4 eq) and 12 (8.2 g, 32.1 mmol, 1.4 eq). The mixture was stirred at room temperature for 18 hrs. Mixture was filtered to separate solid sediment (precipitate) and washed with EA. The filtrate was concentrated. The residue was separated through a column to afford compound 6 5.4 g (77%) as a dark yellow solid. ¹H NMR (300 MHz, CDCl₃) not available.

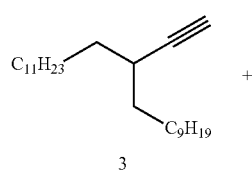

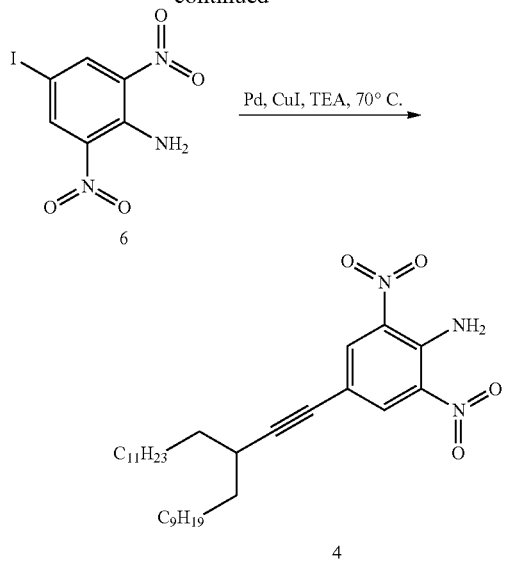

To anhydrous THF (10.0 mL) and TEA (10.0 mL) was added compound 3 (7.4 g, 21.2 mmol, 1.2 eq), compound 6 (5.2 g, 16.7 mmol, 1.0 eq), Pd(dppf)Cl₂ (0.05 g, 0.08 mmol, 0.02 eq), CuI (0.02 g, 0.1 mmol, 0.04 eq). The mixture was degassed under vacuum and purged with N₂ three times. The reaction was stirred at 70° C. for 8.0 hrs. The mixture was cooled down and EA (10 mL) was added to dilute. Filtered off the solid and concentrated the filtrate, separated with a column to afford compound 4 7.5 g (84%) as a yellow solid. ¹H NMR (300 MHz, CDCl₃) δ 7.99 (s, 2H), 2.45 (m, 1H), 1.26-1.55 (m, 40H), 0.87 (t, 6H).

To EtOH (20.0 mL) was added compound 4 (7.5 g, 14.1 mmol, 1.0 eq) and ammonium sulfide (8.6 g 20% water solution, 28.2 mmol, 2.0 eq). The mixture was stirred at 80° C. for 1 hr. Refilled 2.0 eq ammonium sulfide. The received mixture again was stirred at 80° C. for 1 hr. The mixture was concentrated, diluted with EA, washed with water and brine. Organic phase was collected, concentrated and separated through a column to give product 7 6.1 g (87%) as a dark red solid. ¹H NMR (300 MHz, CDCl₃) δ 7.81 (s, 1H), 6.94 (s, 1H), 2.45 (m, 1H), 1.26-1.46 (m, 40H), 0.87 (t, 6H).

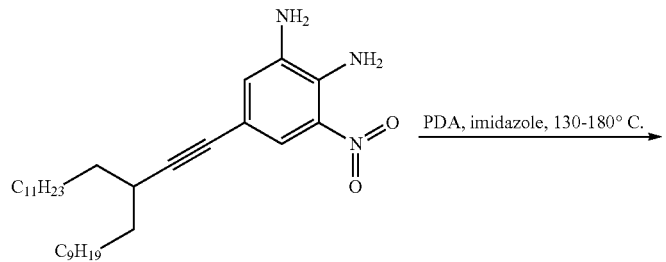

7

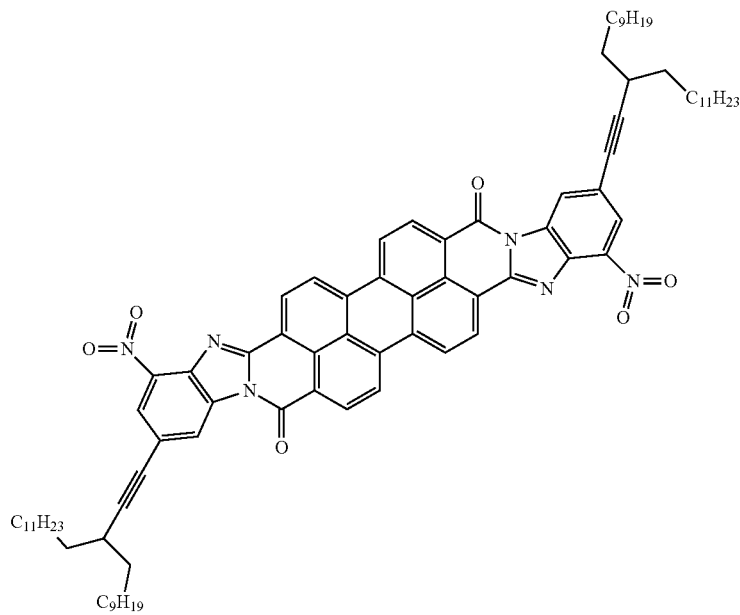

8

To a 25 mL flask was added compound 7 (5.1 g, 10.2 mmol, 2.2 eq), PDA (1.7 g, 4.6 mmol, 1 eq) and imidazole (21 g, 324.5 mmol, 70 eq). The mixture was degassed under vacuum and purged with N₂ three times. The reaction was stirred at 130° C. for 3 hrs and 180° C. for 12 more hrs. The dark purple mixture was cooled down. The solid was washed with water (3×2 mL) and EtOH (3×2 mL), vacuum dried to give product 8 6.2 g (100%) as a dark purple solid. ¹H NMR (300 MHz, CDCl₃) not available.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature described herein, whether preferred or not, may be combined with any other feature described herein, whether preferred or not. In the claims that follow, the indefinite article "A", or "An" refers to a quantity of one or more of the item following the article, except where expressly stated otherwise. As used herein, in a listing of elements in the alternative, the word "or" is used in the logical inclusive sense, e.g., "X or Y" covers X alone, Y alone, or both X and Y together, except where expressly stated otherwise. Two or more elements listed as alternatives may be combined together. The appended claims are not to be interpreted as including means-plus-function limitations, unless such a limitation is explicitly recited in a given claim using the phrase "means for."

What is claimed is:

1. An organic compound characterized by electronic polarizability and having a following general structural formula:

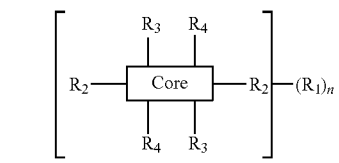

where Core is an aromatic polycyclic conjugated molecule,

R₁ is independently selected from the group consisting of unsubstituted or substituted C₁-C₁₈alkyl, unsubstituted or substituted C₂-C₁₈alkenyl, unsubstituted or substituted C₂-C₁₈alkynyl, and unsubstituted or substituted C₄-C₁₈aryl, fluorinated alkyl, chlorinated alkyl, branched and complex alkyl, branched and complex fluorinated alkyl, branched and complex chlorinated alkyl groups, and any combination thereof, n is 1, 2, 3, 4, 5, 6, 7 or 8, $R_2$ are substitutes located in apex positions, R3 and R4 are substitutes located in side (lateral) positions, and wherein the core has flat anisometric form and the $R_2$ substitutes are selected from hydrogen and electrophilic groups (acceptors) and $R_3$ substitutes and $R_4$ substitutes are independently selected from hydrogen and nucleophilic groups (donors) or vice versa $R_3$ substitutes and $R_4$ substitutes are independently selected from hydrogen and nucleophilic groups (donors), wherein the substitutes $R_2$, $R_3$ and $R_4$ cannot all be hydrogen, and wherein the aromatic polycyclic core is comprised of rylene fragments selected from the structures 1 to 21:

1
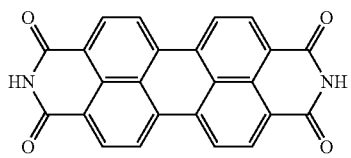

2
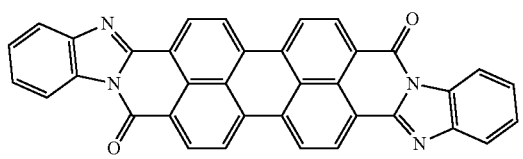

3
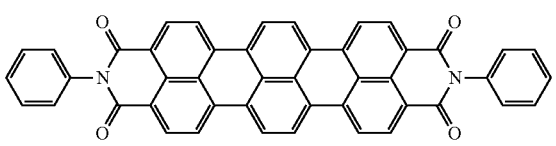

4
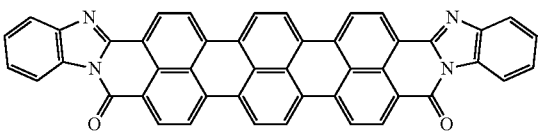

5
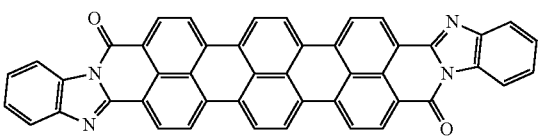

6
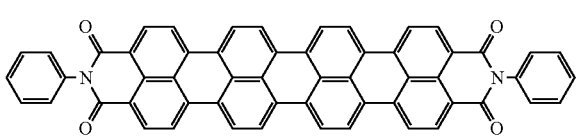

7
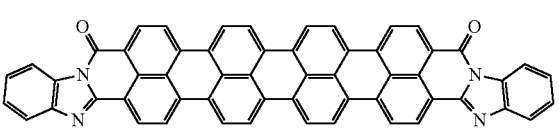

8
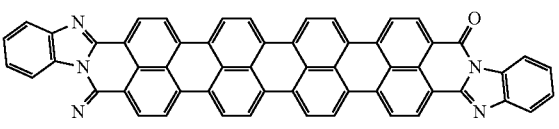

9
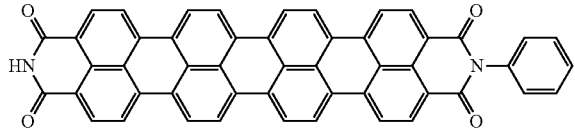

10
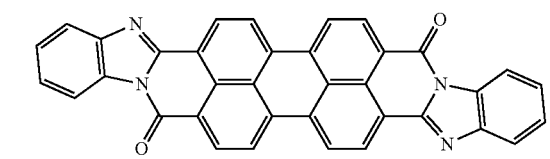

11
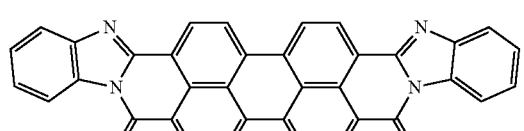

12
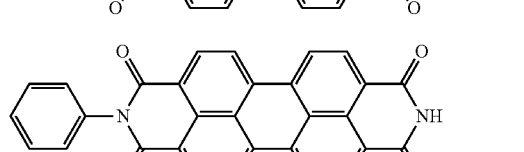

13
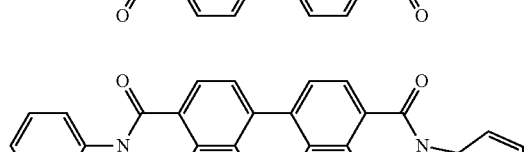

14
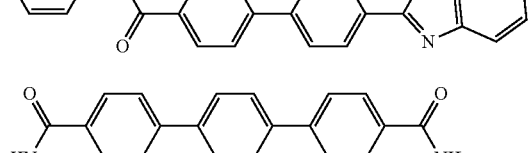

15
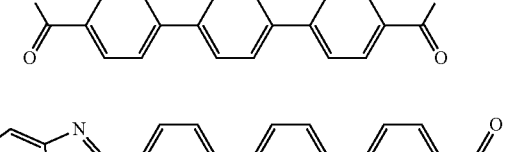

16
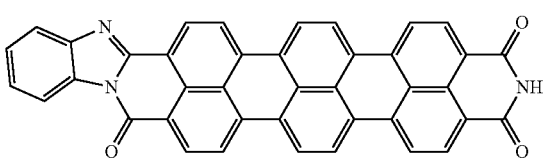

-continued

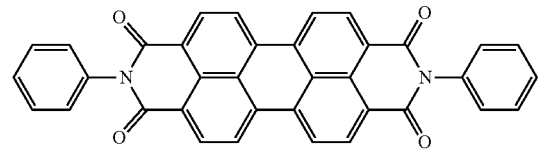
17

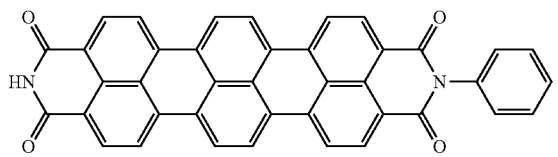
18

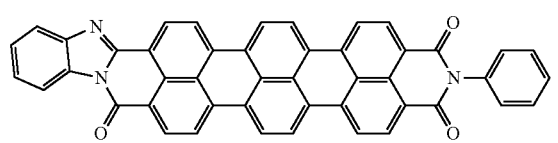
19

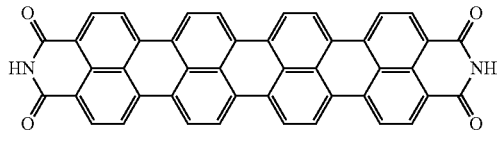
20

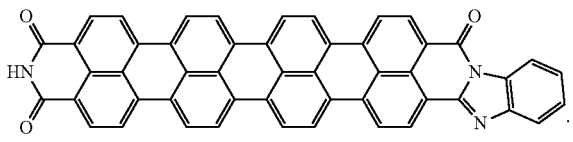
21

2. An organic compound according to claim 1, wherein said $R_1$ groups are isolating groups and are attached to the aromatic polycyclic conjugated core in apex positions and/or side position.

3. An organic compound according to claim 1, wherein the electrophilic groups (acceptors) are selected from —NO$_2$, —NH$_3^+$ and —NR$_3^+$ (quaternary nitrogen salts), counterion Cl$^-$ or Br$^-$, —CHO (aldehyde), —CRO (keto group), —SO$_3$H (sulfonic acids), —SO$_3$R (sulfonates), SO$_2$NH$_2$ (sulfonamides), —COOH (carboxylic acid), —COOR (esters, from carboxylic acid side), —COCl (carboxylic acid chlorides), —CONH$_2$ (amides, from carboxylic acid side), —CF$_3$, —CCl$_3$, —CN, wherein R is radical selected from the list comprising alkyl (methyl, ethyl, isopropyl, tert-butyl, neopentyl, cyclohexyl etc.), allyl (—CH$_2$—CH=CH$_2$), benzyl (—CH$_2$C$_6$H$_5$) groups, and phenyl (+substituted phenyl).

4. An organic compound according to claim 1, wherein the nucleophilic groups (donors) are selected from —O$^-$ (phenoxides, like —ONa or —OK), —NH$_2$, —NHR, NR$_2$, —OH, OR (ethers), —NHCOR (amides, from amine side), —OCOR (esters, from alcohol side), alkyls, —C$_6$H$_5$, vinyls, wherein R is radical selected from the list comprising alkyl (methyl, ethyl, isopropyl, tert-butyl, neopentyl, cyclohexyl etc.), allyl (—CH$_2$—CH=CH$_2$), benzyl (—CH$_2$C$_6$H$_5$) groups, and phenyl (+substituted phenyl).

5. An organic compound according to claim 1, wherein amino groups (—NH$_2$) are used as donors and nitro groups are used as acceptors.

6. A crystal dielectric layer comprising the organic compound according to any of claims 1-2, 3-4, 5.

7. A capacitor comprising a first electrode, a second electrode, and a crystal dielectric layer disposed between said first and second electrodes, wherein said crystal dielectric layer comprises the organic compound according to any of claims 1-2, 3-4, 5, and wherein said crystal dielectric layer comprises supramolecules formed with the aromatic polycyclic conjugated cores, and isotropic insulating sublayers formed with the $R_1$ groups served as the isolating groups.

* * * * *